US008946269B2

(12) United States Patent
Capodanno et al.

(10) Patent No.: US 8,946,269 B2
(45) Date of Patent: Feb. 3, 2015

(54) CRYSTALLINE FORMS OF A FACTOR XA INHIBITOR

(75) Inventors: Vincent R. Capodanno, Rahway, NJ (US); Liam Corcoran, Clonmel (IE); Michael McNevin, Summit, NJ (US); Itzia Zoraida Arroyo, Rahway, NJ (US); Robert M. Wenslow, Rahway, NJ (US); Richard G. Ball, Rahway, NJ (US); Eric L. Margelefsky, Rahway, NJ (US); Timothy K. Maher, Rahway, NJ (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/223,023

(22) Filed: Aug. 31, 2011

(65) Prior Publication Data

US 2012/0071519 A1 Mar. 22, 2012

Related U.S. Application Data

(60) Provisional application No. 61/379,339, filed on Sep. 1, 2010, provisional application No. 61/454,396, filed on Mar. 18, 2011.

(51) Int. Cl.
*A61K 31/44* (2006.01)
*C07D 213/75* (2006.01)

(52) U.S. Cl.
CPC .............. *A61K 31/44* (2013.01); *C07D 213/75* (2013.01)
USPC .......................................................... 514/352

(58) Field of Classification Search
None
See application file for complete search history.

(56) References Cited

U.S. PATENT DOCUMENTS

| 6,140,351 | A | 10/2000 | Arnaiz et al. |
| 6,376,515 | B2 | 4/2002 | Zhu et al. |
| 6,627,646 | B2 | 9/2003 | Bakale et al. |
| 6,835,739 | B2 | 12/2004 | Zhu et al. |
| 6,844,367 | B1 | 1/2005 | Zhu et al. |
| 7,285,565 | B2 | 10/2007 | Zhu et al. |
| 7,314,874 | B2 | 1/2008 | Zhu et al. |
| 7,342,013 | B2 | 3/2008 | Zhu et al. |
| 7,598,276 | B2 * | 10/2009 | Grant et al. .................... 514/352 |
| 8,557,852 | B2 | 10/2013 | Grant et al. |
| 2005/0261346 | A1 | 11/2005 | Zhu et al. |
| 2006/0020039 | A1 | 1/2006 | Zhu et al. |
| 2006/0241153 | A1 | 10/2006 | Zhu et al. |
| 2007/0021472 | A1 | 1/2007 | Zhu et al. |
| 2007/0112039 | A1 | 5/2007 | Grant et al. |
| 2010/0063113 | A1 | 3/2010 | Grant et al. |
| 2010/0197929 | A1 | 8/2010 | Scarborough et al. |
| 2011/0033459 | A1 | 2/2011 | Conley et al. |
| 2012/0083602 | A1 | 4/2012 | Zhu et al. |
| 2012/0095019 | A1 | 4/2012 | Sinha et al. |
| 2013/0064806 | A1 | 3/2013 | Grant et al. |
| 2014/0134151 | A1 | 5/2014 | Lu et al. |

FOREIGN PATENT DOCUMENTS

| WO | WO 2009/042962 | 4/2009 |
| WO | WO 2011084519 | 7/2011 |

OTHER PUBLICATIONS

International Search Report from PCT/US2011/050057, mailed Oct. 14, 2011.
Byrn S. et al. "Pharmaceutical Solids: A Strategic Approach to Regulatory Considerations," Pharmaceutical Research, Kluwer Academic Publishers, New York, US, vol. 12, No. 7, pp. 945-954, Jul. 1, 1995.
International Search Report and Written Opinion from PCT/US2011/050058, mailed Oct. 28, 2011.
U.S. Appl. No. 13/612,597, filed Sep. 12, 2012, Zhu, et al.
Bastin et al. Salt Selection and Optimisation Procedures for Pharmaceutical New Chemical Entities. Organic Process Research & Development, 2000, vol. 4, p. 427-435.
Berge et al. Pharmaceutical salts. Journal of pharmaceutical Sciences, 1977, vol. 66, No. 1, p. 1-19.
Brittain et al., Polymorphism in Pharmaceutical Solids. NY: Marcel Dekker, Inc., 1999, pp. 1-2, 183-226.
Caira, Crystalline Polymorphism of Organic Compounds. Topics in current chemistry; 1998, vol. 198, p. 163-208.
CMU Pharmaceutical Polymorphism, 2002, Internet pp. 1-3 (printout Apr. 3, 2008).
Concise Encyclopedia Chemistry, NY: Walter de Gruyter Berlin, 1994, pp. 872-873.
Doelker. Crystalline modifications and polymorphous changes during drug manufacture. English translation of Ann. Pharm. Fr., 2002, 60:161-176, pp. 1-39.
Doelker. Caracteres physiocochemiques des principes actifs leurs consequences sur la faisabilite et la stabilite des formes galeniques. English translation of S.T.P. Pharma Pratiques, 1999, 9(5), 399-409, pp. 1-33.
Gould et al. Recent Advances in the Discovery and Development of Direct Coagulation Factor Xa Inhibitors. *Current Pharmaceutical Design*, 2003, 9, 2337-2347.
Grant, D. Theory and Origin of Polymorphism, *Polymorphism in Pharmaceutical Solids*. Ed. H.G. Brittain, 1999, pp. 1-10.
Jain et al. Polymorphism in Pharmacy. Indian Drugs, 1986, 23(6), pp. 315-329.
Muzaffer et al. Polymorphism and drug availability. J of Pharmacy (Lahore), 1979, 9(1), pp. 59-66.
Rouhi, Maureen. The Right Stuff from research and development to the clinic, getting drug crystals right is full of pitfalls. Chemical & Engineering News, 2003, pp. 32-5.
Otsuka et al. Effect of polymorphic forms of bulk powders on pharmaceutical properties of carbamazepine granules. Chem. Pharm. Bull. 1999, 47(6), pp. 852-856.

(Continued)

*Primary Examiner* — Craig Ricci
(74) *Attorney, Agent, or Firm* — Sheppard Mullin Richter & Hampton LLP

(57) ABSTRACT

Provided herein are crystalline forms of a maleate salt of betrixaban, compositions and methods of preparation or use thereof.

8 Claims, 17 Drawing Sheets

(56) References Cited

OTHER PUBLICATIONS

Rowland et al. Clinical Pharmacokinetics—concepts and applications, 1996, p. 123.

Silverman. The Organic Chemistry of Drug Design and Drug Action, NY: Academic Press, 1993, pp. 72-76.

Singhal et al., Drug polymorphism and dosage from design: a practical perspective. Advanced Drug Delivery Reviews, 2004, 56, pp. 335-347.

Taday et al. Using Terahertz pulse spectroscopy to study the crystalline structure of a drug: a case study of the polymorphs of ranitidine hydrochloride. J of Pharmaceutical Sciences, 2003, 92(4), pp. 831-838.

Toschi et al. Inhibitors of propagation of coagulation: factors V and X. British Journal of Clinical Pharmacology, 2011, 72(4), pp. 563-80. Abstract Only.

U.S. Pharmacopia #23, National Formulary, 1995, #18, pp. 1843-1844.

Vippagunta et al. Crystalline solids. *Advanced Drug Delivery Reviews*, 2001, 48, 3-26.

Walenga et al. Factor Xa Inhibitors. Methods in Molecular Medicine™ Anticoagulants, Antiplatelets, and Thrombolytics. Shaker A. Mousa, Ed. *Humana Press Inc.*, 2004, 95-117.

International Search Report and Written Opinion from PCT/US2006/043635, mailed Feb. 27, 2002.

Morissette et al., "High-throughput Crystallization: Polymorphs, Salts, Co-crystals and Solvates of Pharmaceutical Solids," *Adv. Drug Delivery Review*, 56(3): 275-300 (2004).

Norris, Experimental Organic Chemistry. McGraw-Hill Book Company, Inc. $2^{nd}$ Edition, (1924).

Office Action for U.S. Appl. No. 13/612,476 mailed May 9, 2013.

Office Action for U.S. Appl. No. 13/612,476 mailed Aug. 22, 2013.

\* cited by examiner

CRYSTALLINE FORMS OF A FACTOR XA INHIBITOR

CROSS REFERENCE TO RELATED APPLICATIONS

This application claims the benefit under 35 U.S.C. §119 (e) of U.S. Provisional Application Ser. Nos. 61/379,339 filed on Sep. 1, 2010, and 61/454,396 filed on Mar. 18, 2011, which are hereby incorporated by reference in their entirety.

BACKGROUND OF THE INVENTION

1. Field of the Invention

Provided herein are crystal polymorphs of a factor Xa inhibitor and compositions and methods thereof.

2. State of the Art

Factor Xa is a serine protease, the activated form of its precursor factor X, and a member of the calcium ion binding, gamma carboxyglutamic acid (GLA)-containing, vitamin K dependent, blood coagulation factors. Factor Xa appears to have a single physiologic substrate, namely prothrombin. Since one molecule of factor Xa may be able to generate greater than 1000 molecules of thrombin (Mann, et al., *J. Thrombosis. Haemostasis* 1: 1504-1514, 2003), direct inhibition of factor Xa as a way of indirectly inhibiting the formation of thrombin has been considered an efficient anticoagulant strategy.

Several classes of small molecule factor Xa inhibitors have been reported, for example, in U.S. Pat. Nos. 7,521,470, 7,696,352, and 7,763,608, U.S. Patent Application Publication Nos. 2007/0066615, 2008/0293704, and 2008/0051578, all of which are incorporated by reference in their entirety.

U.S. Pat. No. 6,376,515 B2 discloses a specific factor Xa inhibitor compound identified in Example 206, which is also disclosed in U.S. Pat. No. 6,835,739 B2 as Example 206 and herein identified as betrixaban. The structure of betrixaban is represented by Formula I:

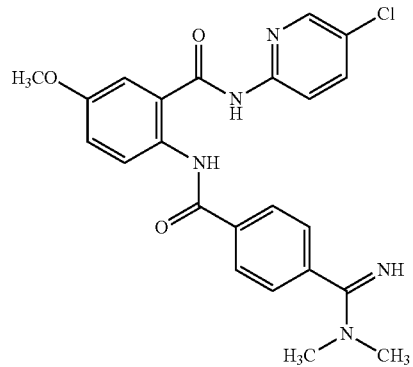

I

In addition, U.S. Pat. No. 7,598,276 (the '276 patent) describes salts and a crystalline polymorph of a maleate salt of betrixaban (also referred to as Form I). U.S. Pat. Nos. 6,376,515, 6,835,739 and 7,598,276 are incorporated by reference in their entirety.

SUMMARY

In one aspect, there is provided crystalline polymorphs of the maleate salt of betrixaban, which salt is represented by Formula II:

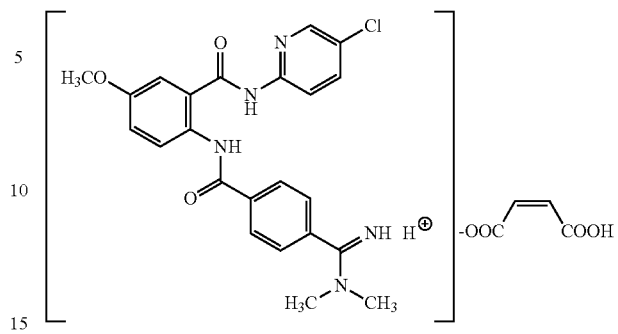

II

In one embodiment, there is provided Form II, a crystalline form which exhibits an X-ray powder diffraction pattern having at least the following approximate characteristic peak locations: 5.0, 9.7, 10.1, 15.3, 17.5, and 19.6 degrees 2θ. In another embodiment, the X-ray powder diffraction pattern has at least six, or eight, or ten, or all of the approximate characteristic peak locations selected from 5.0, 9.7, 10.1, 14.6, 15.3, 17.5, 18.0, 18.7, 19.6, 19.2, 22.0, 22.6, 23.0, 23.7, 24.5, 26.5, 26.9, 29.2, 29.5, 30.4, and 35.0 degrees 2θ. In one embodiment, the approximate characteristic peaks will have a deviation of up to about 0.05 degrees 2θ. In another embodiment, the X-ray powder diffraction pattern is approximate to the X-ray powder diffraction pattern shown in FIG. 2 or 3. In one embodiment, Form II is an anhydrate.

In another embodiment, there is provided Form III, another crystalline form of the maleate salt of Formula II which exhibits an X-ray powder diffraction pattern having at least the following approximate characteristic peak locations: 15.1, 2.2, 4.9, 17.4, 10.0, and 22.4 degrees 2θ. In another embodiment, the X-ray powder diffraction pattern has at least six, or eight, or ten, or all of the approximate characteristic peak locations selected from 15.1, 2.2, 4.9, 17.4, 10.0, 22.4, 26.5, 2.9, 24.6, 19.4, and 24.2 degrees 2θ. In one embodiment, Form III is a hemihydrate. 2θ. In one embodiment, the approximate characteristic peaks will have a deviation of up to about 0.05 degrees 2θ. In another embodiment, the X-ray powder diffraction pattern is approximate to the top X-ray powder diffraction pattern shown in FIG. 12.

In another aspect, there is provided a method for preparing Form II or Form III. In some embodiments, the method is for preparing Form II, which method comprises heating a composition comprising the salt of Formula II:

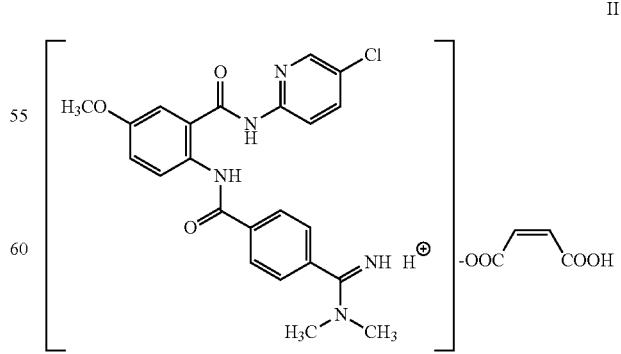

II in a solvent comprising water and optionally ethanol to a temperature of at least about 50° C. to obtain a solution, and cooling the solution to at or below about 20° C. but above the freezing temperature of the solvent.

In some embodiments, the method is for preparing Form II, which method comprises heating a composition comprising betrixaban free base and at least one equivalent of maleic acid in a solvent comprising water and optionally ethanol to a temperature of about 45° C. to about 60° C., addition of a seed crystal of Form II, and cooling the solution to at or below about 30° C. but above the freezing temperature of the solvent.

In another aspect, there is provided a method of preparing betrixaban, comprising reacting Compound C:

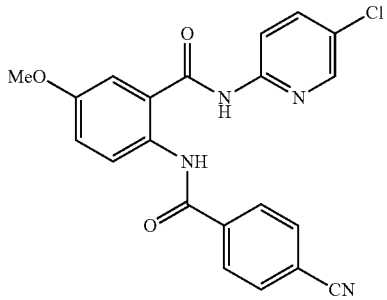

C with dimethylamide lithium (LiN(CH$_3$)$_2$) under reaction conditions wherein the dimethylamide lithium is added over a period of no less than 3 hours at a temperature of between about 8° C. and about 12° C.

In another aspect, there is provided a pharmaceutical composition for preventing or treating a condition characterized by undesired thrombosis in a subject comprising a pharmaceutically acceptable carrier and a therapeutically effective amount of one or more of the polymorphs of the maleate salt of betrixaban provided herein. In other embodiments, the pharmaceutical composition is suitable for oral delivery. In one embodiment, the pharmaceutical composition is in tablet form. In another embodiment, the pharmaceutical composition is in capsule form. In yet another embodiment, the pharmaceutical composition is in lozenge form. In other embodiments, the pharmaceutical composition is in a form suitable for infusion, injection, or transdermal delivery.

In yet another aspect, there is provided a method for preventing or treating a condition characterized by undesired thrombosis in a subject comprising administering to the subject a therapeutically effective amount of Form II or Form III.

In some embodiments, there is provided a method for preventing or treating thrombosis in a subject in need thereof, comprising administering to the subject a therapeutically effective amount of Form II or Form III.

In some embodiments, the condition is, or the thrombosis is associated with a condition selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, thromboembolic stroke, systemic embolism, ischemic stroke, venous thromboembolism, non-valvular atrial fibrillation, transient ischemic attacks, venous thrombosis, deep venous thrombosis, pulmonary embolus, coagulopathy, disseminated intravascular coagulation, thrombotic thrombocytopenic purpura, thromboanglitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

In some embodiments, the polymorphs are useful in:
prevention of stroke in atrial fibrillation patients (Stroke Prevention in Atrial Fibrillation (SPAF));
prevention of thrombosis in medically ill patients, such as acute medically ill patients;
prevention and treatment of deep vein thrombosis;
prevention and treatment of thrombosis in patients with hip or knee surgery;
prevention of arterial thrombosis in acute coronary syndrome patients; and/or
secondary prevention of acute coronary syndrome, myocardial infarction, stroke or other thrombotic events in patients who have had a prior event (e.g., including but not limited to a myocardial infarction or a stroke event).

In still another aspect, there is provided a method for inhibiting the coagulation of a blood sample comprising the step of contacting the sample with the betrixaban maleate crystalline Form II or Form III.

DETAILED DESCRIPTION OF THE INVENTION

I. Definitions

Figure 1:
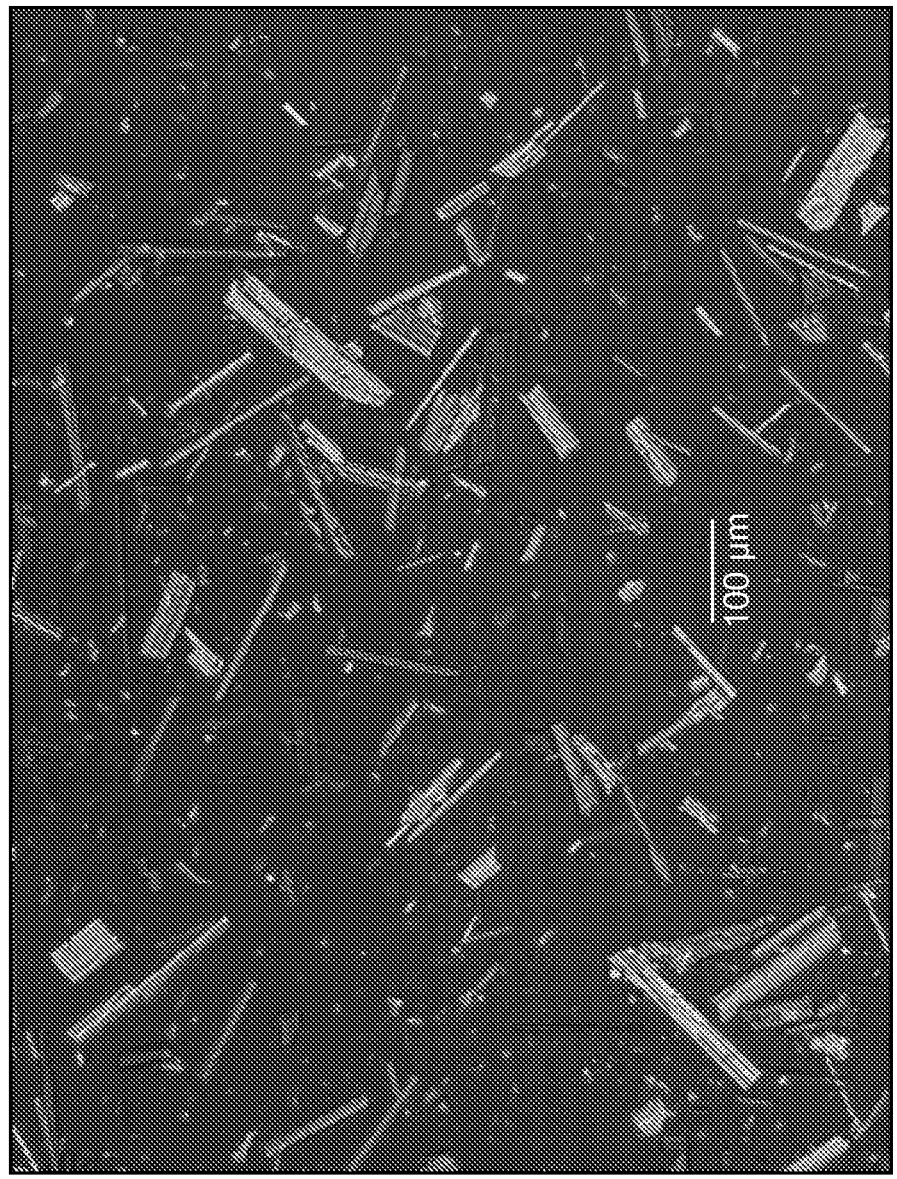
FIG. 1 provides an optical micrograph of a sample of Form II, (scale bar=100 μM), which is shown to be anisotropic and consists of blade-shaped crystals with no observed agglomerates. The optical micrograph of Form II may change, for example, after milling, heating, or cooling.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, the term "polymorph" refers to the crystalline form of a substance that is distinct from another crystalline form of the substance but that are the same compound or salt of a compound. Crystalline forms can be characterized by their crystalline structure (X-ray diffraction pattern), their thermal properties (as determined by DSC and TGA), stability, solubility, etc. The X-ray diffraction pattern is presented as characteristic peaks ±0.2, ±0.1, ±0.05 or ±0.02 degrees. When two X-ray diffraction patterns have at least 4, preferably at least 6, 8, or 10 2θ° peaks, or more preferably all peaks, that do not vary more than ±0.2, ±0.1 or ±0.02 degrees, it is deemed that the X-ray diffraction patterns are substantially the same. The different polymorphic forms of the same compound can have an impact on one or more physical properties, such as stability, solubility, melting point, bulk density, flow properties, bioavailability, etc. One skilled in the art would readily identify a polymorph of a compound based on the characteristic 2θ° peaks of an X-ray diffraction pattern of the polymorph. In some embodiments, characteristic peaks are those having a relative intensity of about 25% or more. In some embodiments, characteristic peaks are those that have a relative intensity of about 10% or more. In some embodiments, characteristic peaks are those that have a relative intensity of about 5% or more.

The term "hydrate" refers to a crystalline form that has an amount of water bound in the crystal lattice. "Hemihydrate" is a hydrate wherein the number of water molecules in the crystalline form is half of the number of the compound molecules or the number of the salt pairs of a salt of the compound in the crystalline form. When water molecules included in the lattice lie next to other water molecules of adjoining unit cells forming channels, the hydrate is called a "channel hydrate."

The term "anhydrate" or "anhydrous polymorph" refers to a crystalline form that does not have water bound in the crystal lattice. However, the crystals may contain trace amount of water or other solvents not bound in the crystal lattice. Hydrates and anhydrates may show different physical properties like habitus, stability, dissolution rate and bioavailability as known for polymorphs.

The term "unit cell" refers to the smallest structural component of a crystal, which is stacked in three-dimensional space to describe the crystal. The unit cell can be defined by its lattice parameters such as the length of the cell edges and the angles between them. The positions of the atoms inside the unit cell can be described by the set of atomic positions measured from a lattice point.

The term "treatment" or "treating" means any treatment of a disease or disorder in a subject, such as a mammal, including:
  preventing or protecting against the disease or disorder, that is, causing the clinical symptoms not to develop;
  inhibiting the disease or disorder, that is, arresting or suppressing the development of clinical symptoms; and/or
  relieving the disease or disorder that is, causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "therapeutically effective amount" refers to that amount of a polymorph, typically delivered as a pharmaceutical composition, that is sufficient to effect treatment, as defined herein, when administered to a subject in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can be determined readily by one of ordinary skill in the art.

As used herein, the term "condition" refers to a disease state for which the compounds, salts, compositions and methods provided herein are being used.

As used herein, the term "a medically ill patient" refers to a patient who is admitted to the hospital or a nursing facility for a nonsurgical illness who requires prophylaxis for venous thromboembolic disease, or who is expected to be hospitalized for at least 6 days due to an acute medical condition.

In some embodiments, a medically ill patient meets one of the following risk criteria (i.e., 1 through 4), and either at least two additional risk factors as outlined below or has a D-dimer of more than two times the upper limit of normal.
1. Acutely decompensated heart failure, New York Heart Association (NYHA) class III or IV;
2. Acute respiratory failure without the need for prolonged (<=2 days) respiratory support;
3. Acute infection without septic shock;
4. Acute rheumatic disorders (including acute lumbar pain, sciatica, vertebral compression, acute arthritis of the legs, or an episode of inflammatory bowel disease).

The additional risk factors for venous thromboembolism (VTE) include:
Age>75 years;
Previous history of VTE that required anticoagulant therapy;
Expected marked immobilization>=3 days (Level 1—bedrest without bathroom privileges);
Obesity (Body Mass Index (BMI)>30 for men or 28.6 for women);
Varicose veins or chronic venous insufficiency;
Lower extremity paresis;
Central venous catheterization;
Hormone therapy (antiandrogen, estrogen or, selective estrogen receptor modulators (SERMs));
Chronic heart failure;
Chronic respiratory failure;
Active collagen vascular disease;
Acute infectious disease contributing to current hospitalization;
Erythropoeisis stimulating agents;
Inflammatory bowel disease;
Venous compression (tumor, hematoma or arterial anomaly);
Nephrotic syndrome; and
Inherited or acquired thrombophilia.

As used herein, the term "primary prevention" refers to identifying the risk factors that can lead to cardiovascular disease followed by intervention.

As used herein, the term "secondary prevention" refers to early detection of established coronary artery disease followed by initiation/intervention with aggressive risk reduction therapy such as lipid management, diabetes, weight management, antiplatelet, and anticoagulant therapy.

As used herein, the term "blood sample" refers to whole blood taken from a subject, or any fractions of blood including plasma or serum.

As used herein, the term "patient" or "subject" refers to mammals and includes humans and non-human mammals. In particular embodiments herein, the patient or subject is a human.

As used herein, the term "reaction conditions" refers to the details under which a chemical reaction proceeds. Examples of reaction conditions include, but are not limited to, one or more of the following: reaction temperature, solvent, pH, pressure, reaction time, mole ratio of reactants, the presence of a base or acid, or catalyst, etc. Reaction conditions may be named after the particular chemical reaction in which the conditions are employed, such as, coupling conditions, hydrogenation conditions, acylation conditions, reduction conditions, salt forming conditions, crystallization conditions, etc. Reaction conditions for known reactions are generally known to those skilled in the art.

The term "about" when used before a numerical value indicates that the value may vary within reasonable range, such as ±5%, ±1%, and ±0.2%. When "about" is used before a 2θ° peak of an XRPD, it indicates that the 2θ° value may vary ±0.2, ±0.1, ±0.05 or ±0.02 degrees.

II. Polymorphs

In one aspect, there is provided polymorphs of a maleate salt of betrixaban. In one embodiment, the maleate salt is represented as Formula II:

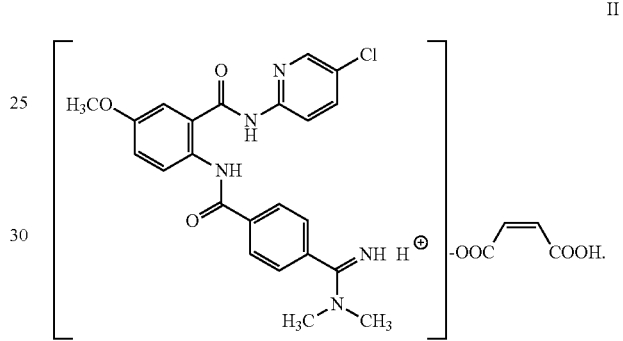

U.S. Pat. No. 7,598,276 (the '276 patent) describes a crystalline polymorph of the maleate salt of betrixaban (Form I). Provided herein are crystalline polymorph Form II and Form III of the maleate salt of betrixaban of Formula II.

a. Form II

A thermodynamically stable betrixaban maleate salt crystalline polymorph, Form II, has been discovered. Unlike Form I, which is kinetically favored and tends to form at moderate-temperatures in uncontrolled (unseeded) conditions, Form II has unexpected improved stability and allows for the maleate salt of betrixaban to be manufactured consistently and reliably in the same form, especially at the crystallization conditions in which it is generated. Form II has been found to be stable at different temperatures and in different-solvents tested. Form II was unexpectedly discovered when crystallization was performed at a higher temperature. It is contemplated that the unexpectedly high thermodynamic stability of Form II provides better purity, a more reliable pharmacokinetic profile, efficacy and/or safety profile. Further, Form II has demonstrated superior handling and flow of both the compound and drug product granulations, compared to Form I. Form II possesses a similar in vitro dissolution profile as Form I.

Form II has a higher melting point of 213° C. as compared with the melting point of 201° C. exhibited by Form I.

In some embodiments, Form II is an anhydrate. In some embodiments, Form II is characterized by properties including one or more of the following as described in details herein:
its X-ray powder diffraction pattern (XRPD);
its infrared spectrum (IR);
its differential scanning calorimetry (DSC);

its thermogravimetric analysis (TGA);
its vapor sorption curve,
solid state NMR, and
crystal structure, such as unit cell structure.

In one embodiment, Form II exhibits an X-ray powder diffraction pattern having the following approximate characteristic peak locations: 5.0, 9.7, 10.1, 15.3, 17.5, and 19.6 degrees 2θ. In another embodiment, the X-ray powder diffraction pattern has at least four, six, eight or ten of the approximate characteristic peak locations of 5.0, 9.7, 10.1, 14.6, 15.3, 17.5, 18.0, 18.7, 19.2, 19.6, 22.0, 22.6, 23.0, 23.7, 24.5, 26.5, 26.9, 29.2, 29.5, 30.4 and 35.0 degrees 2θ. In another embodiment, the X-ray powder diffraction pattern has at least four, six, eight or ten of the approximate characteristic peak locations of 5.0, 9.5, 9.7, 10.1, 14.6, 15.3, 17.5, 18.0, 18.7, 19.2, 19.6, 22.0, 22.6, 23.0, 23.7, 24.5, 26.5, 26.9, 29.2, 29.5, 30.4 and 35.0 degrees 2θ. In another embodiment, the X-ray powder diffraction pattern has at least four, six, eight or ten of the approximate characteristic peak locations of 15.3, 5.0, 10.1, 17.5, 9.7, 19.6, 24.5, 18.6, 18.0, 14.5, 22.6, 22.9, 23.0, 22.1, 29.2, 26.5, 24.8, 18.3, and 21.6 degrees 2θ. It is contemplated that the approximate characteristic peaks will have a deviation of up to about 0.1 or 0.05 degrees 2θ.

Figure 2:
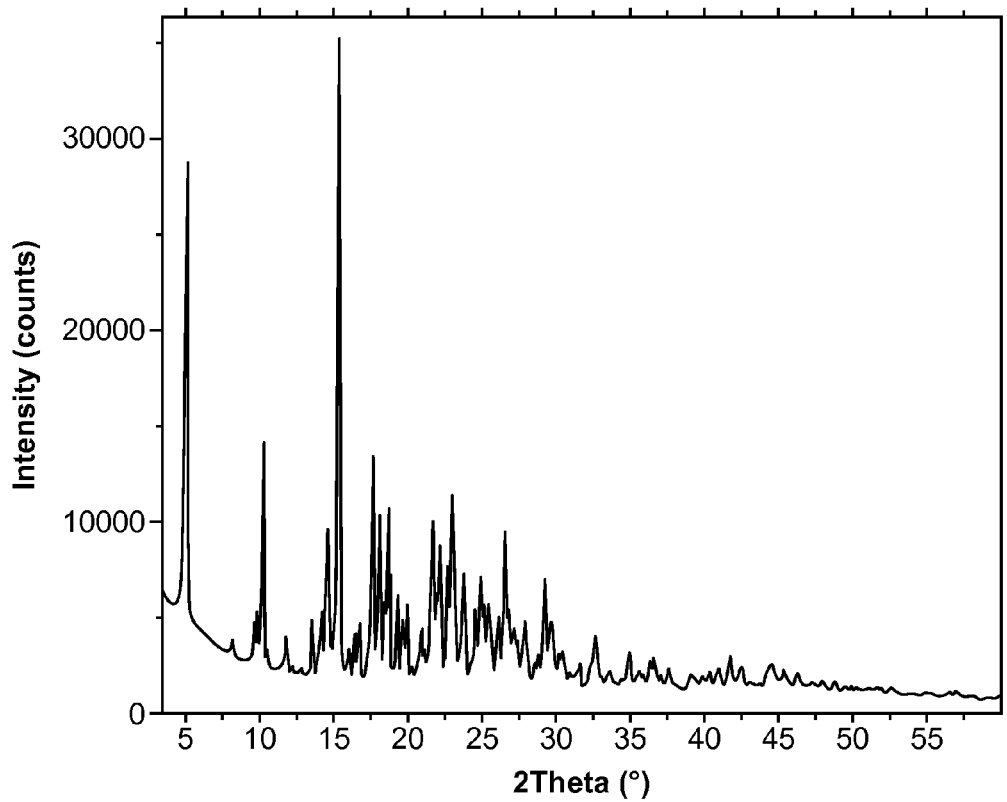
FIG. 2 provides an X-ray powder diffraction (XRPD) pattern of Form II.
Figure 3:
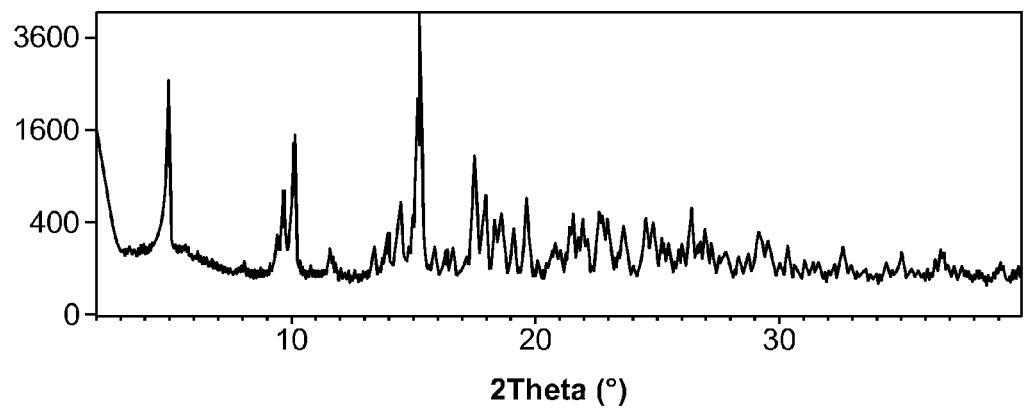
FIG. 3 provides an expanded XRPD pattern of Form II.
Figure 4:
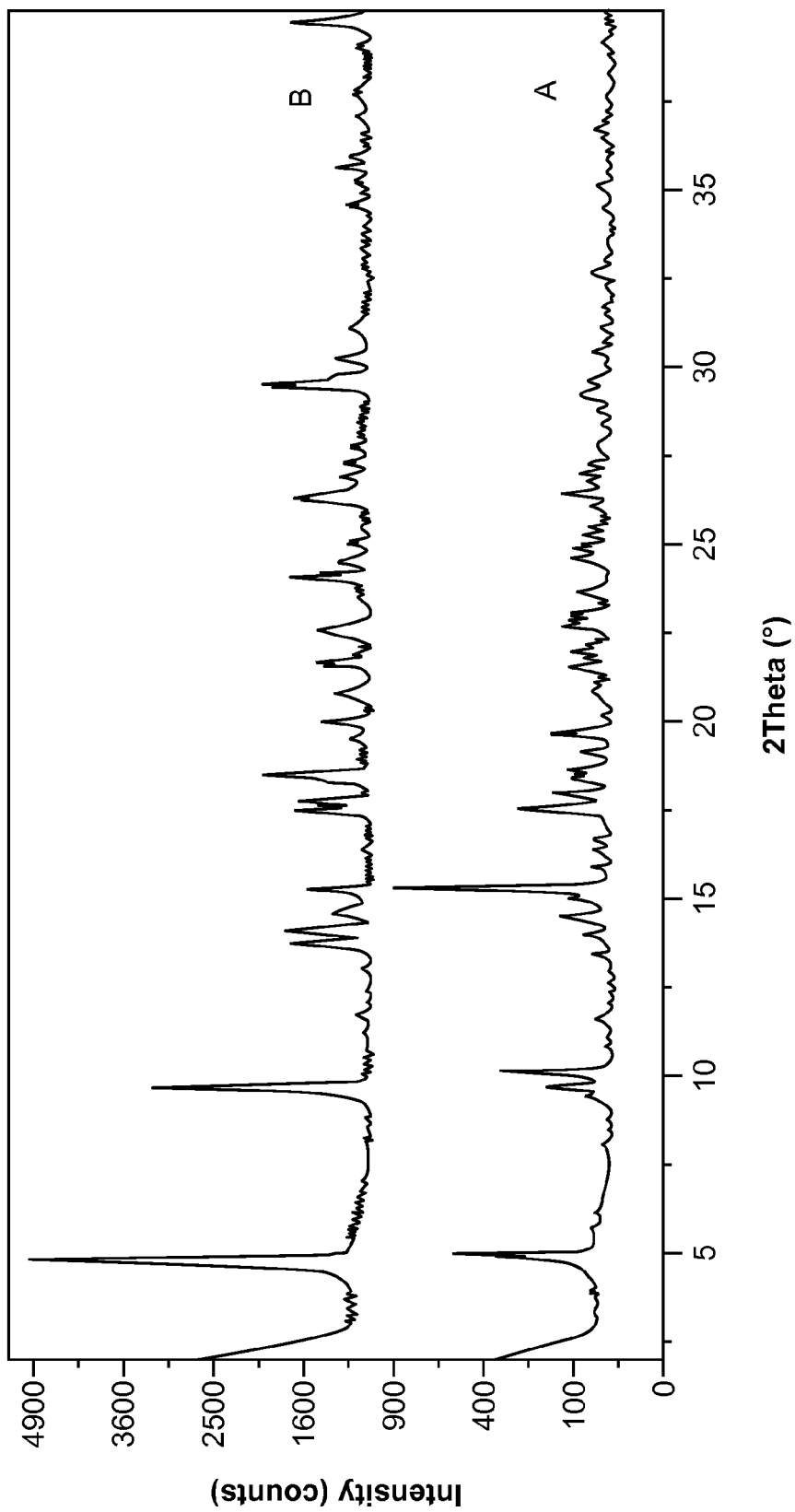
FIG. 4 provides comparison of an XRPD pattern of Form II (A) with an XRPD pattern of Form I described in the '276 patent (B).

In yet another embodiment, the X-ray powder diffraction pattern is approximate to the X-ray powder diffraction pattern shown in FIG. 2 or 3.

In one embodiment, the X-ray powder diffraction pattern comprises at least the peaks listed in Table 1 or 2 with a height of at or above 500 counts (cts). In another embodiment, the X-ray powder diffraction pattern comprises at least the peaks listed in Table 1 or 2 with a height of at or above 200 cts. In yet another embodiment, the X-ray powder diffraction pattern comprises at least the peaks listed in Table 1 or 2 with a height of at or above 100 cts. In another embodiment, the X-ray powder diffraction pattern comprises at least the peaks listed in Table 1 or 2 with a height of at or above 50 cts. In yet another embodiment, the X-ray powder diffraction pattern comprises or consists of all peaks listed in Table 1 or Table 2. One skilled in the art would understand that the height of the peak and relative intensity are reliant on many experimental conditions including the type of instrument, beam intensity, length of acquisition time, sample preparation, etc.

TABLE 1

Peak Position, d-Spacing and Peak Height of Form II of a First Sample

| Peak Position [°2θ] | Relative Intensity [%] | d-Spacing [Å] | Height [counts] |
|---|---|---|---|
| 5.0 | 43 | 17.62 | 1869.9 |
| 9.5 | 6.2 | 9.30 | 267.2 |
| 9.7 | 15 | 9.11 | 664.1 |
| 10.1 | 27 | 8.72 | 1166.0 |
| 11.6 | 1.3 | 7.61 | 57.4 |
| 14.0 | 4.4 | 6.31 | 190.8 |
| 14.6 | 4.6 | 6.09 | 200.6 |
| 15.3 | 100 | 5.80 | 4338.3 |
| 15.9 | 1.6 | 5.56 | 71.3 |
| 16.4 | 2.1 | 5.41 | 93.0 |
| 16.7 | 1.5 | 5.32 | 64.1 |
| 17.5 | 41 | 5.06 | 1777.2 |
| 18.0 | 7.2 | 4.92 | 314.0 |
| 18.4 | 4.4 | 4.83 | 190.0 |
| 18.7 | 6.2 | 4.76 | 267.0 |
| 19.2 | 5.7 | 4.62 | 247.9 |
| 19.6 | 20 | 4.52 | 856.1 |
| 20.8 | 4.3 | 4.26 | 187.6 |
| 21.1 | 3.4 | 4.22 | 147.3 |
| 21.6 | 3.1 | 4.11 | 135.0 |

TABLE 1-continued

Peak Position, d-Spacing and Peak Height of Form II of a First Sample

| Peak Position [°2θ] | Relative Intensity [%] | d-Spacing [Å] | Height [counts] |
|---|---|---|---|
| 22.0 | 5.3 | 4.03 | 230.1 |
| 22.6 | 10 | 3.93 | 433.7 |
| 23.0 | 6.6 | 3.87 | 284.7 |
| 23.7 | 4.7 | 3.75 | 203.0 |
| 24.5 | 11 | 3.63 | 466.9 |
| 24.9 | 4 | 3.58 | 183.3 |
| 25.5 | 2 | 3.49 | 88.1 |
| 26.1 | 2.6 | 3.42 | 114.1 |
| 26.5 | 6.4 | 3.37 | 276.3 |
| 26.9 | 7.2 | 3.31 | 312.0 |
| 27.3 | 2.2 | 3.26 | 94.1 |
| 27.8 | 2.4 | 3.21 | 102.1 |
| 28.48 | 1.5 | 3.14 | 64.9 |
| 28.7 | 2 | 3.11 | 88.2 |
| 29.2 | 7.2 | 3.06 | 311.2 |
| 29.5 | 5.7 | 3.025 | 247.2 |
| 30.4 | 4.4 | 2.94 | 193.0 |
| 31.1 | 1 | 2.88 | 44.4 |
| 31.6 | 1.6 | 2.83 | 68.6 |
| 32.7 | 2.7 | 2.74 | 119.3 |
| 34.3 | 1.2 | 2.61 | 54.1 |
| 35.0 | 4.6 | 2.57 | 200.8 |
| 36.3 | 2.2 | 2.47 | 96.4 |
| 36.7 | 2.5 | 2.45 | 107.9 |
| 39.1 | | 2.30 | 75.8 |

TABLE 2

Peak Position, d-Spacing and Peak Height of Form II of a Second Sample

| Peak Position [°2θ] | Relative Intensity [%] | FWHM [°2θ] | d-spacing [Å] | Tip width [°2θ] | Height [counts] |
|---|---|---|---|---|---|
| 15.3 | 100 | 0.1004 | 5.81 | 0.102 | 7126.9 |
| 5.0 | 60.35 | 0.0669 | 17.67 | 0.068 | 4301.3 |
| 10.1 | 36.03 | 0.0836 | 8.74 | 0.085 | 2567.8 |
| 17.5 | 19.93 | 0.1171 | 5.06 | 0.119 | 1420.2 |
| 9.7 | 13.69 | 0.1004 | 9.12 | 0.102 | 975.6 |
| 19.6 | 12.41 | 0.1171 | 4.54 | 0.119 | 884.5 |
| 24.5 | 10.19 | 0.1004 | 3.64 | 0.102 | 725.9 |
| 18.6 | 9.4 | 0.0836 | 4.77 | 0.085 | 669.9 |
| 18.0 | 8.32 | 0.0836 | 4.93 | 0.085 | 593.2 |
| 14.5 | 7.94 | 0.0669 | 6.10 | 0.068 | 565.8 |
| 22.6 | 7.73 | 0.1171 | 3.94 | 0.119 | 551.1 |
| 22.9 | 6.58 | 0.102 | 3.89 | 0.085 | 468.7 |
| 23.0 | 6.55 | 0.0836 | 3.87 | 0.085 | 466.8 |
| 22.1 | 6.5 | 0.1673 | 4.02 | 0.17 | 463.5 |
| 29.2 | 6.47 | 0.1004 | 3.06 | 0.102 | 461.2 |
| 26.5 | 5.75 | 0.1171 | 3.37 | 0.119 | 409.6 |
| 24.8 | 5.14 | 0.0669 | 3.59 | 0.068 | 366.4 |
| 18.3 | 5.08 | 0.1004 | 4.84 | 0.102 | 361.8 |
| 21.6 | 4.9 | 0.0836 | 4.11 | 0.085 | 349.5 |
| 29.6 | 4.33 | 0.1171 | 3.02 | 0.119 | 308.2 |
| 19.2 | 3.86 | 0.1004 | 4.63 | 0.102 | 275.4 |
| 23.7 | 3.86 | 0.1338 | 3.75 | 0.136 | 275.1 |
| 34.9 | 3.62 | 0.0836 | 2.57 | 0.085 | 257.9 |
| 26.9 | 3.24 | 0.1338 | 3.31 | 0.136 | 231.0 |
| 14.0 | 3.03 | 0.0836 | 6.31 | 0.085 | 215.6 |
| 36.6 | 3.01 | 0.2007 | 2.46 | 0.204 | 214.8 |
| 26.0 | 2.72 | 0.1004 | 3.42 | 0.102 | 193.8 |
| 25.5 | 2.68 | 0.1004 | 3.49 | 0.102 | 190.9 |
| 20.8 | 2.66 | 0.1338 | 4.27 | 0.136 | 189.7 |
| 16.4 | 2.55 | 0.1004 | 5.41 | 0.102 | 181.8 |
| 16.7 | 2.51 | 0.1004 | 5.32 | 0.102 | 179.1 |
| 32.7 | 2.19 | 0.2342 | 2.74 | 0.238 | 155.8 |
| 27.3 | 2.13 | 0.0669 | 3.27 | 0.068 | 152.0 |
| 27.8 | 2.13 | 0.1004 | 3.21 | 0.102 | 151.8 |
| 13.4 | 2.08 | 0.1004 | 6.58 | 0.102 | 148.3 |
| 19.8 | 2.06 | 0.1004 | 4.47 | 0.102 | 147.0 |

TABLE 2-continued

Peak Position, d-Spacing and Peak Height
of Form II of a Second Sample

| Peak Position [°2θ] | Relative Intensity [%] | FWHM [°2θ] | d-spacing [Å] | Tip width [°2θ] | Height [counts] |
|---|---|---|---|---|---|
| 30.4 | 2.02 | 0.2342 | 2.94 | 0.238 | 143.7 |
| 36.3 | 2 | 0.1338 | 2.48 | 0.136 | 142.4 |
| 21.0 | 1.94 | 0.1004 | 4.22 | 0.102 | 138.4 |
| 11.6 | 1.85 | 0.1004 | 7.63 | 0.102 | 131.6 |
| 28.7 | 1.76 | 0.1338 | 3.11 | 0.136 | 125.2 |
| 15.9 | 1.72 | 0.1171 | 5.58 | 0.119 | 122.6 |
| 31.5 | 1.52 | 0.1338 | 2.84 | 0.136 | 108.6 |
| 31.0 | 1.12 | 0.1338 | 2.89 | 0.136 | 79.5 |
| 28.4 | 1.01 | 0.1338 | 3.14 | 0.136 | 71.9 |
| 34.3 | 1.01 | 0.2007 | 2.61 | 0.204 | 72.0 |
| 39.0 | 0.94 | 0.1338 | 2.31 | 0.136 | 66.9 |
| 37.1 | 0.92 | 0.1338 | 2.42 | 0.136 | 65.9 |
| 39.5 | 0.88 | 0.1004 | 2.28 | 0.102 | 62.6 |
| 8.1 | 0.84 | 0.1004 | 10.94 | 0.102 | 59.7 |
| 37.5 | 0.73 | 0.2007 | 2.40 | 0.204 | 52.0 |

In one embodiment, Form II is characterized by the X-ray diffraction pattern shown in FIG. 2 or 3.

In one embodiment, Form II is an anhydrous crystalline form. In some embodiments, it is a white solid with high melting point (213° C.). It is the most thermodynamically stable form known to date and is monotropically related to the polymorph Form I disclosed in the '276 patent. It absorbs up to 1% water at 95% RH.

Figure 5A:
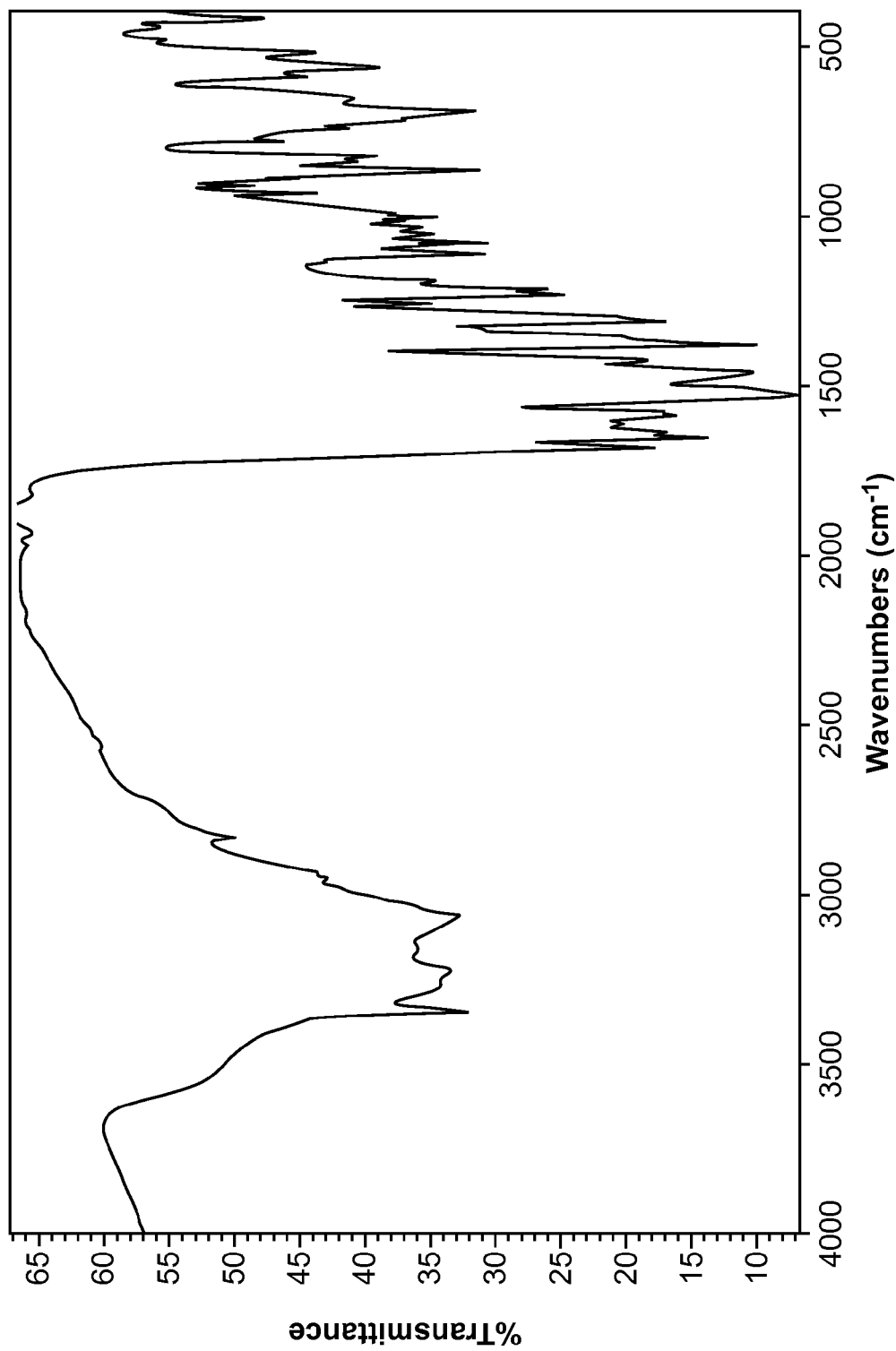
FIGS. 5A and 5B show infrared spectra of two samples of Form II.
Figure 5B:
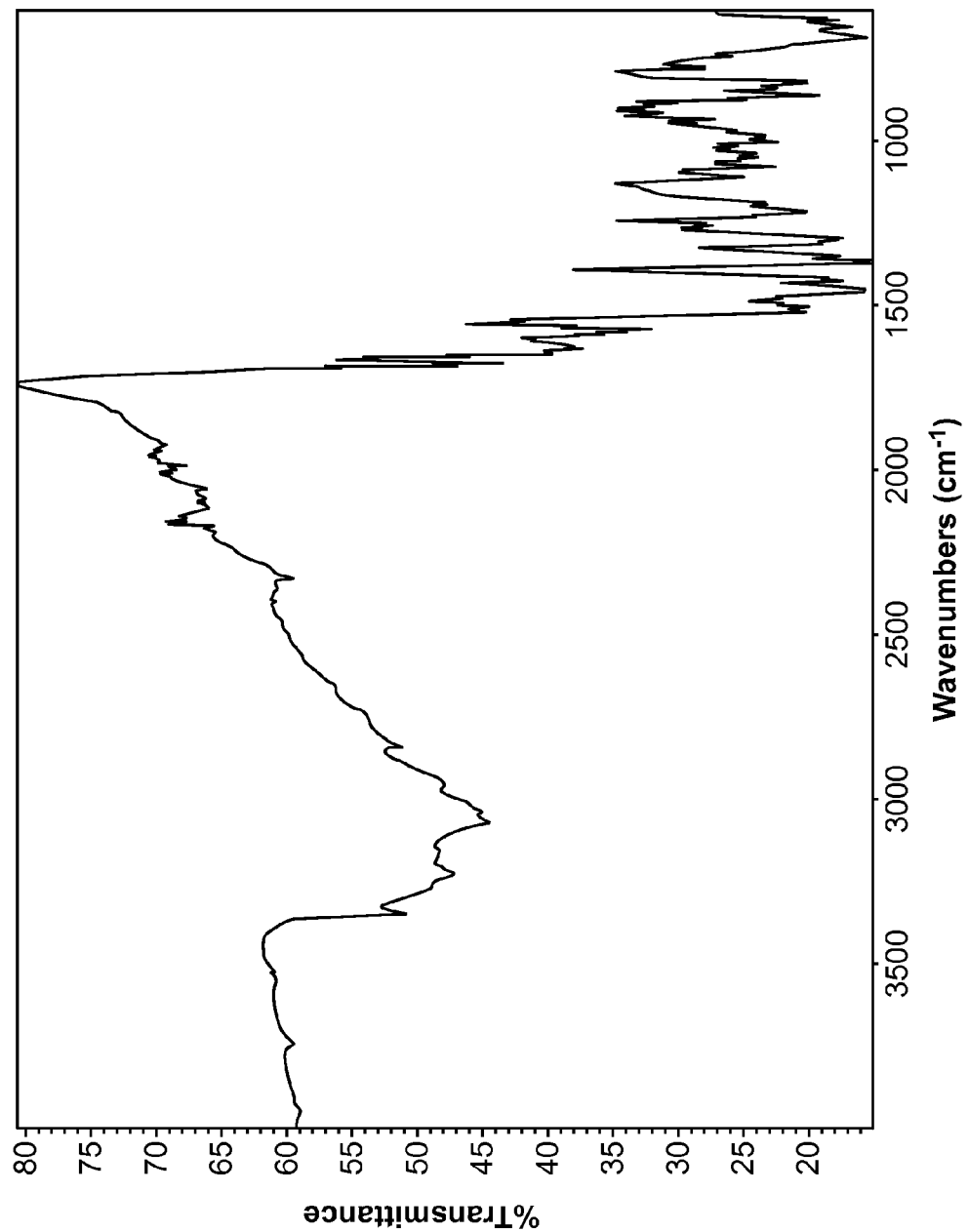

In some embodiments, Form II is characterized by an infrared spectrum substantially the same as FIG. 5A or FIG. 5B. In some embodiments, Form II is characterized by the infrared spectrum shown in FIG. 5A or FIG. 5B.

Figure 6:
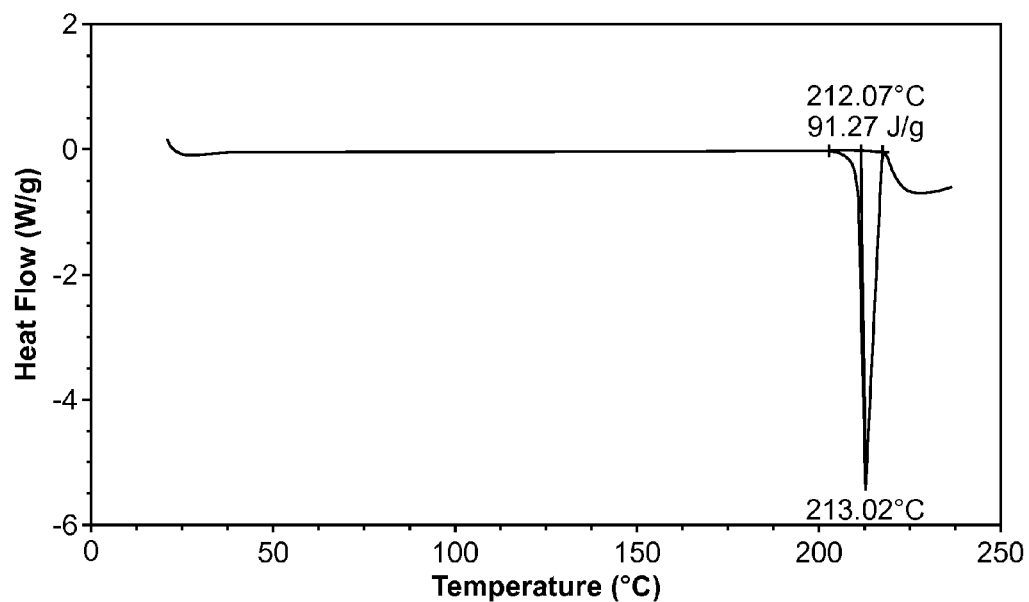
FIG. 6 provides a differential scanning calorimetry (DSC) curve of Form II.

In some embodiments, Form II is characterized by a differential scanning calorimetry (DSC) substantially the same as FIG. 6. In some embodiments, Form II is characterized by the differential scanning calorimetry (DSC) shown in FIG. 6.

Figure 7:
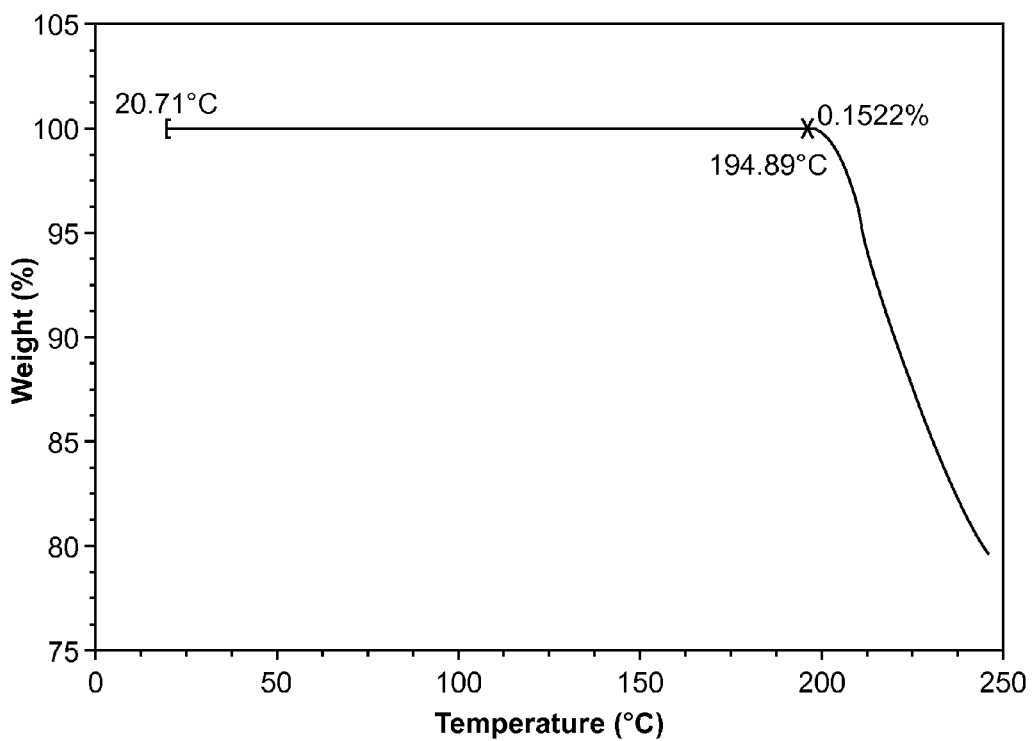
FIG. 7 provides a thermogravimetric analysis (TGA) curve of Form II, during which analysis Form II exhibited 0.152% weight loss from room temperature to about 195° C.

In some embodiments, the polymorph Form II is characterized by a thermogravimetric analysis (TGA) curve substantially the same as FIG. 7. In some embodiments, Form II is characterized by the thermogravimetric analysis (TGA) curve shown in FIG. 7.

Figure 8:
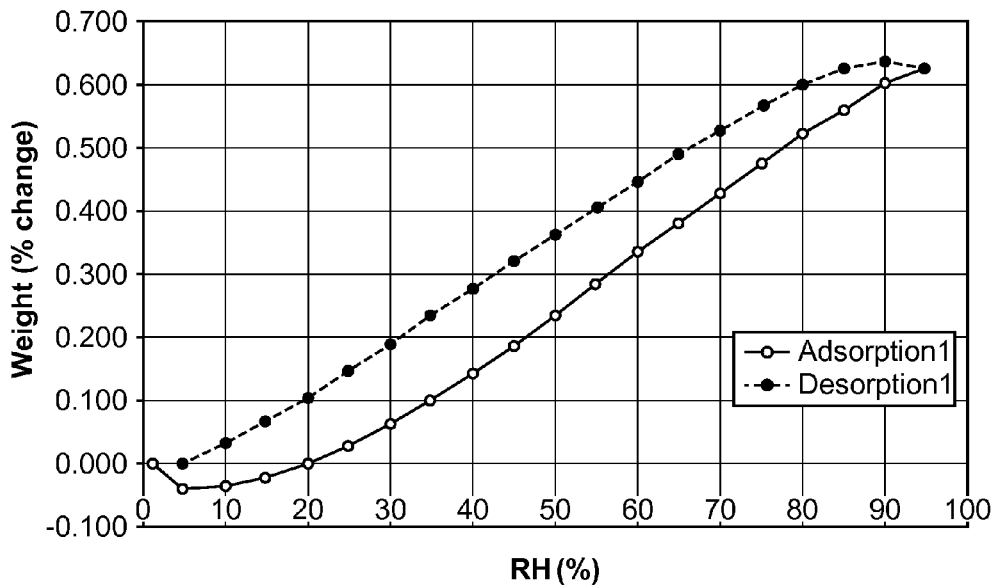
FIG. 8 provides a vapor sorption analysis of Form II crystallized from dry ethanol, in which analysis Form II exhibited continuous weight gain from 1% to up to 95% relative humidity (RH). The sample adsorbed 0.6% water up to 95% RH. Identical XRPD pattern was obtained before and after vapor sorption analysis.
Figure 9:
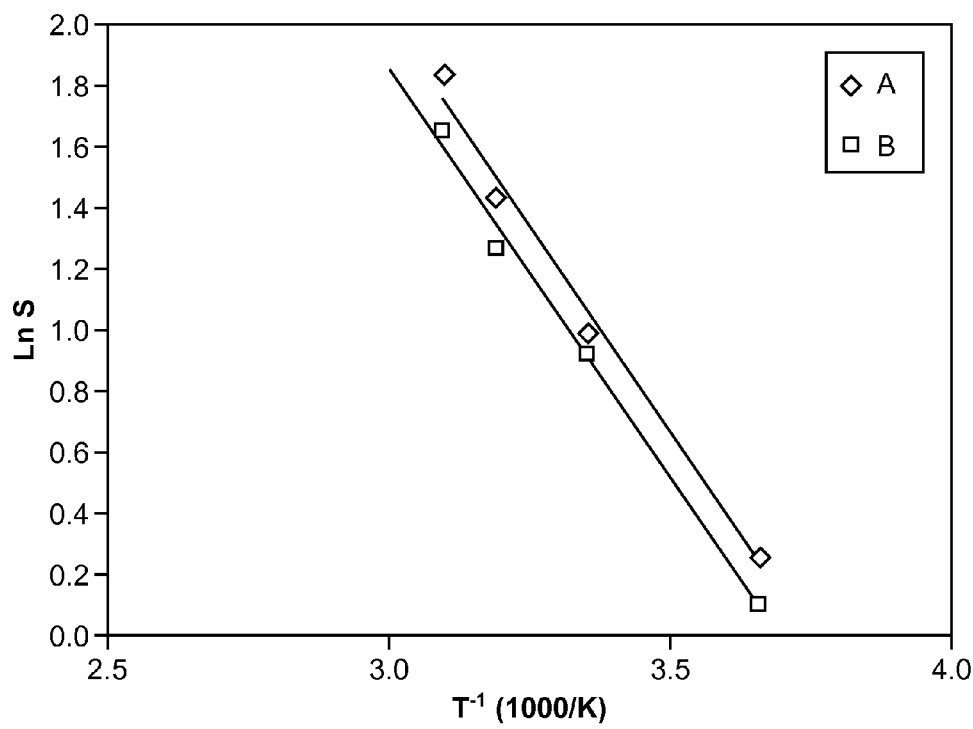
FIG. 9 provides a Van't Hoff solubility plots for Form I (A) and Form II (B).
Figure 10:
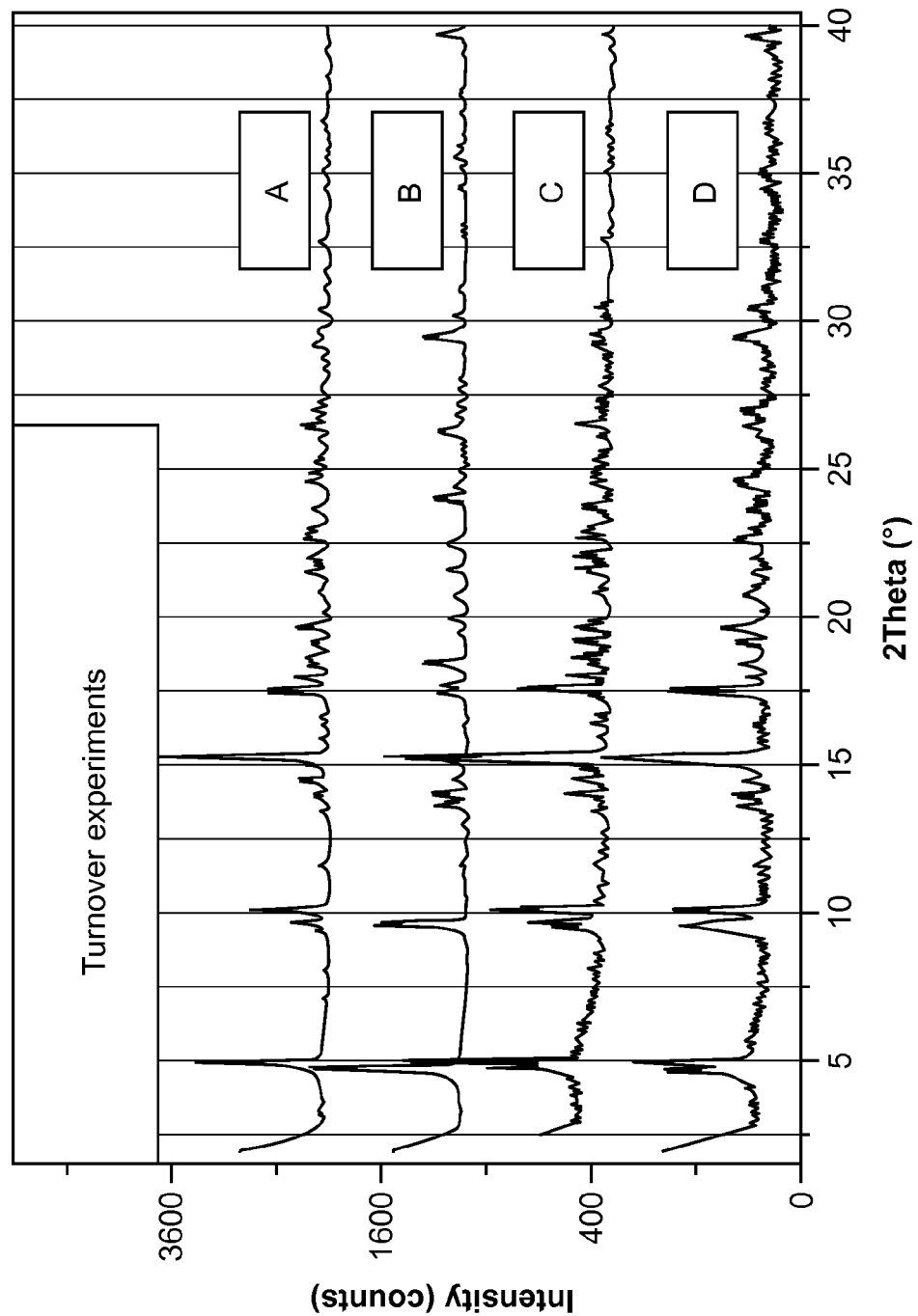
FIG. 10 provides XRPD patterns from turnover experiments. A is an XRPD of Form II. B is an XRPD of Form I. D represents an XRPD pattern 1 hour after Form I and Form II were mixed in EtOH. C represents an XRPD pattern 1 day after Form I and Form II were mixed in EtOH. It is shown that after one hour of both forms being slurred together, the diffraction peaks of Form II became more intense than the diffraction peaks of Form I. After one day, the diffraction peaks of Form II were significantly more intense than the peaks of Form I. Data show that Form II remains physically and chemically stable at 25° C. and 60% RH and at 40° C. and 75% RH for at least 6 months.
Figure 15:
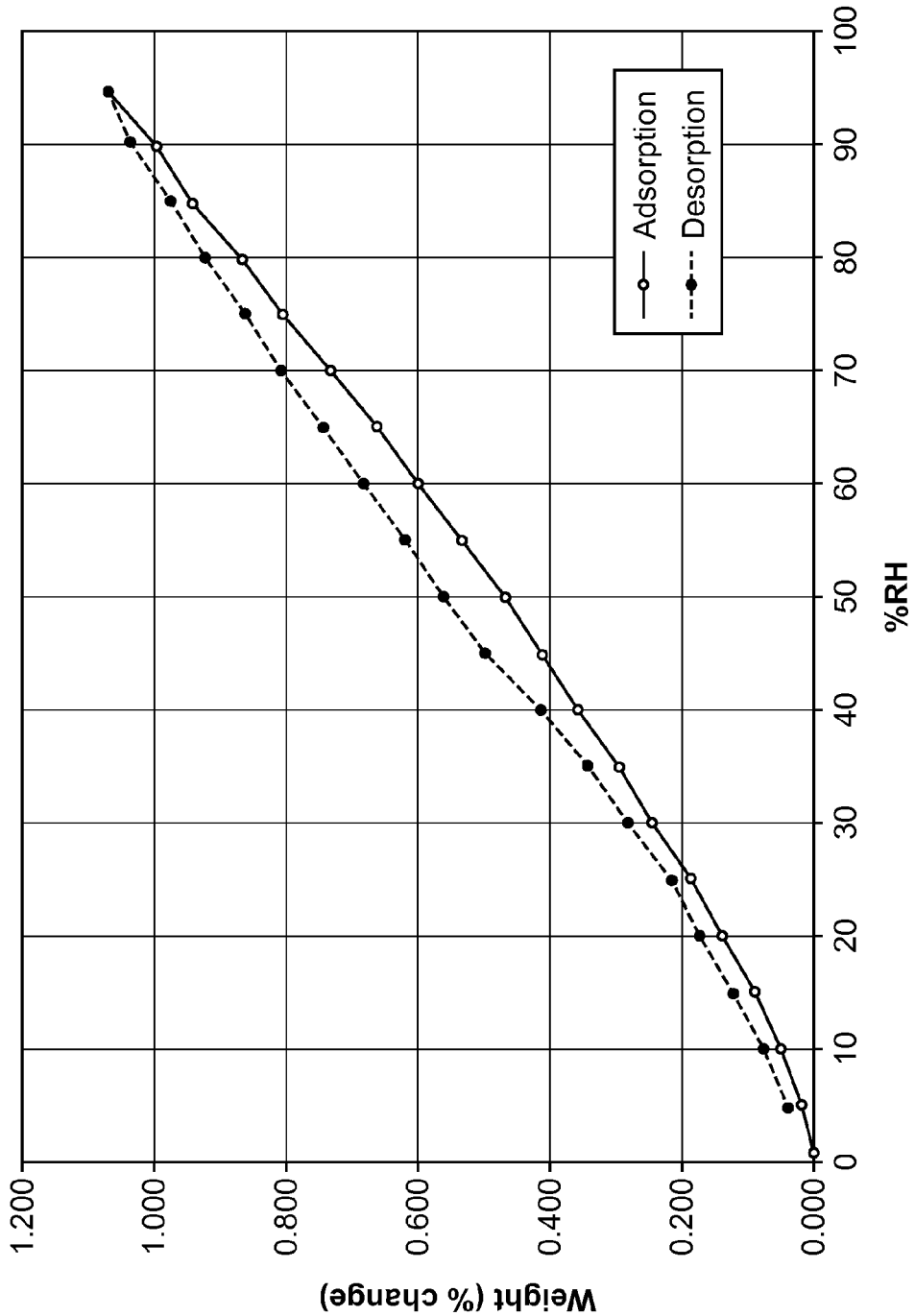
FIG. 15 provides a Vapor Sorption analysis for Form II prepared from 25:75 ethanol/water through Form III. Water intake is about 1% at 95% RH, which is similar to the sample crystallized from dry ethanol shown in FIG. 8.

In some embodiments, Form II is characterized by a vapor sorption curve substantially the same as FIG. 8 or 15. In some embodiments, Form II is characterized by the vapor sorption curve shown in FIG. 8 or 15.

In some embodiments, Form II has a crystal structure characterized by a unit cell containing two independent salt pairs of betrixaban and maleic acid wherein the imine N (N2 in FIG. 11) is protonated and forms an ionic H-bond to the maleic acid counter-ion. In one embodiment, the crystal structure of Form II comprises a number of other hydrogen-bonding interactions resulting in a complex network. In some embodiments, the crystal structure is characterized by a unit cell structure with the following cell parameters at 100 K and 273 K:

| Temperature (K) | a (Å) | b (Å) | c (Å) | α (°) | β (°) | γ (°) | V (Å³) |
|---|---|---|---|---|---|---|---|
| 100 | 8.284 | 18.082 | 18.681 | 71.22 | 86.76 | 89.69 | 2645 |
| 273 | 8.419 | 18.113 | 18.73 | 71.14 | 86.71 | 89.31 | 2699 |

Figure 11:
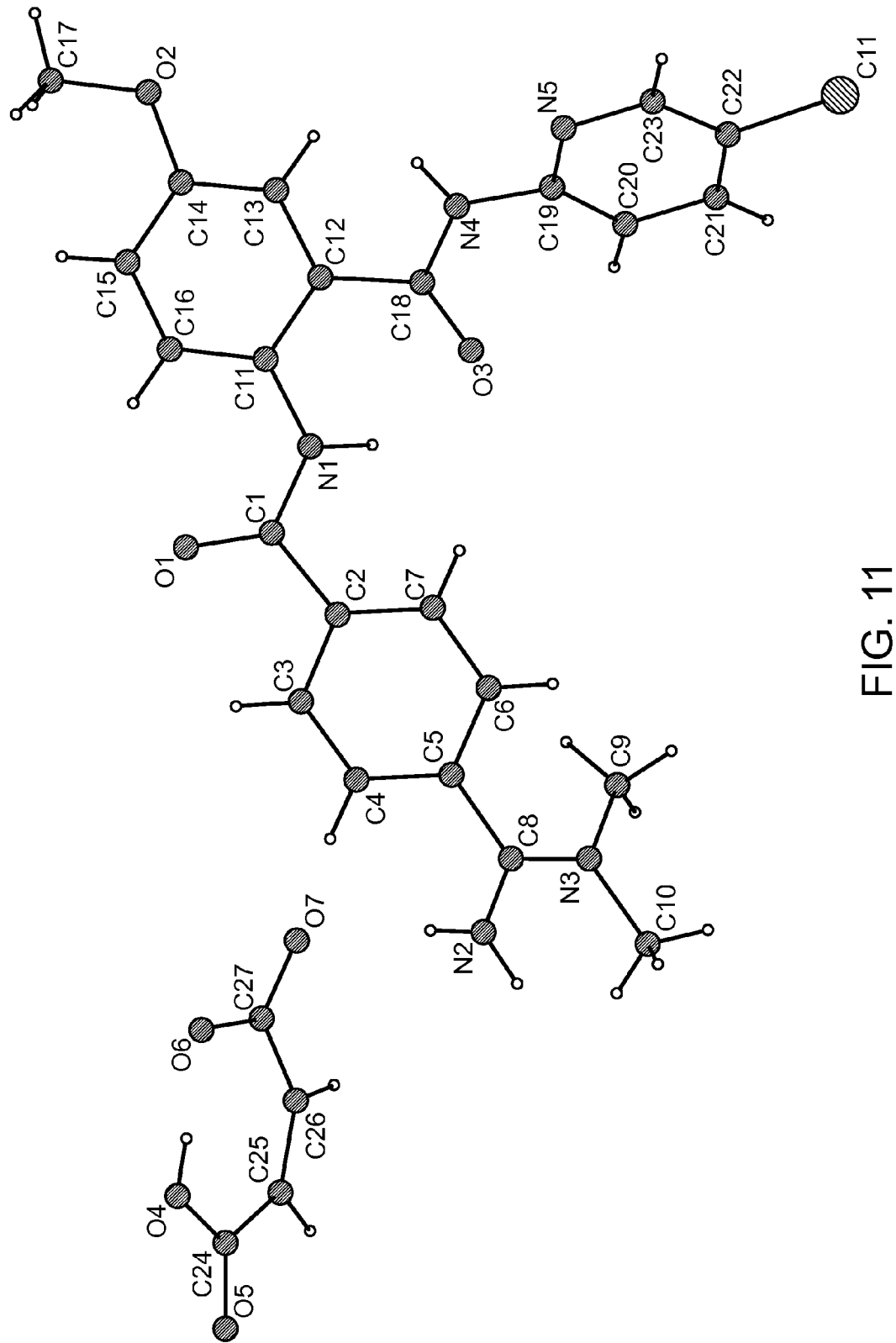
FIG. 11 provides a perspective view of Form II generated from the crystallographic coordinates.
Figure 12:
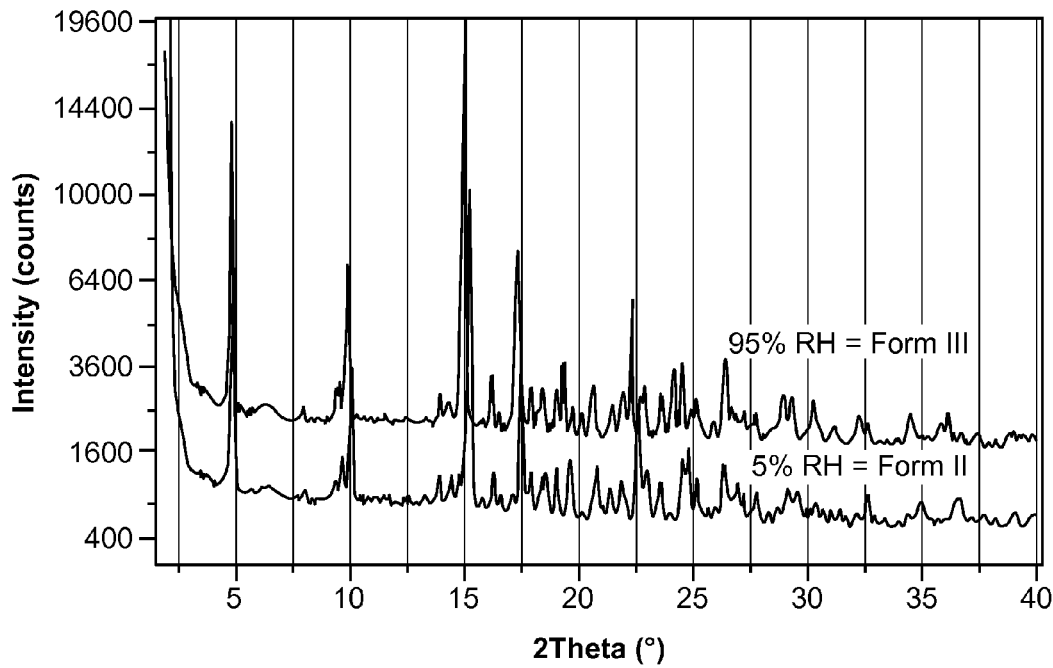
FIG. 12 provides XRPD patterns of Form II and Form III.
Figure 13:
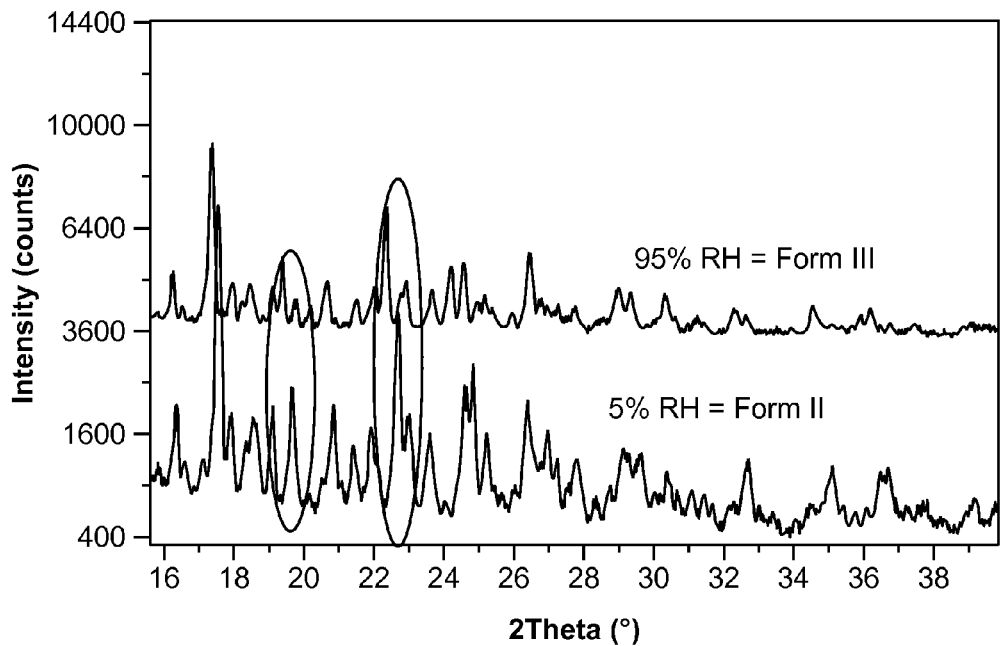
FIG. 13 provides an expanded view of the XRPD patterns of the polymorphs shown in FIG. 12.
Figure 14:
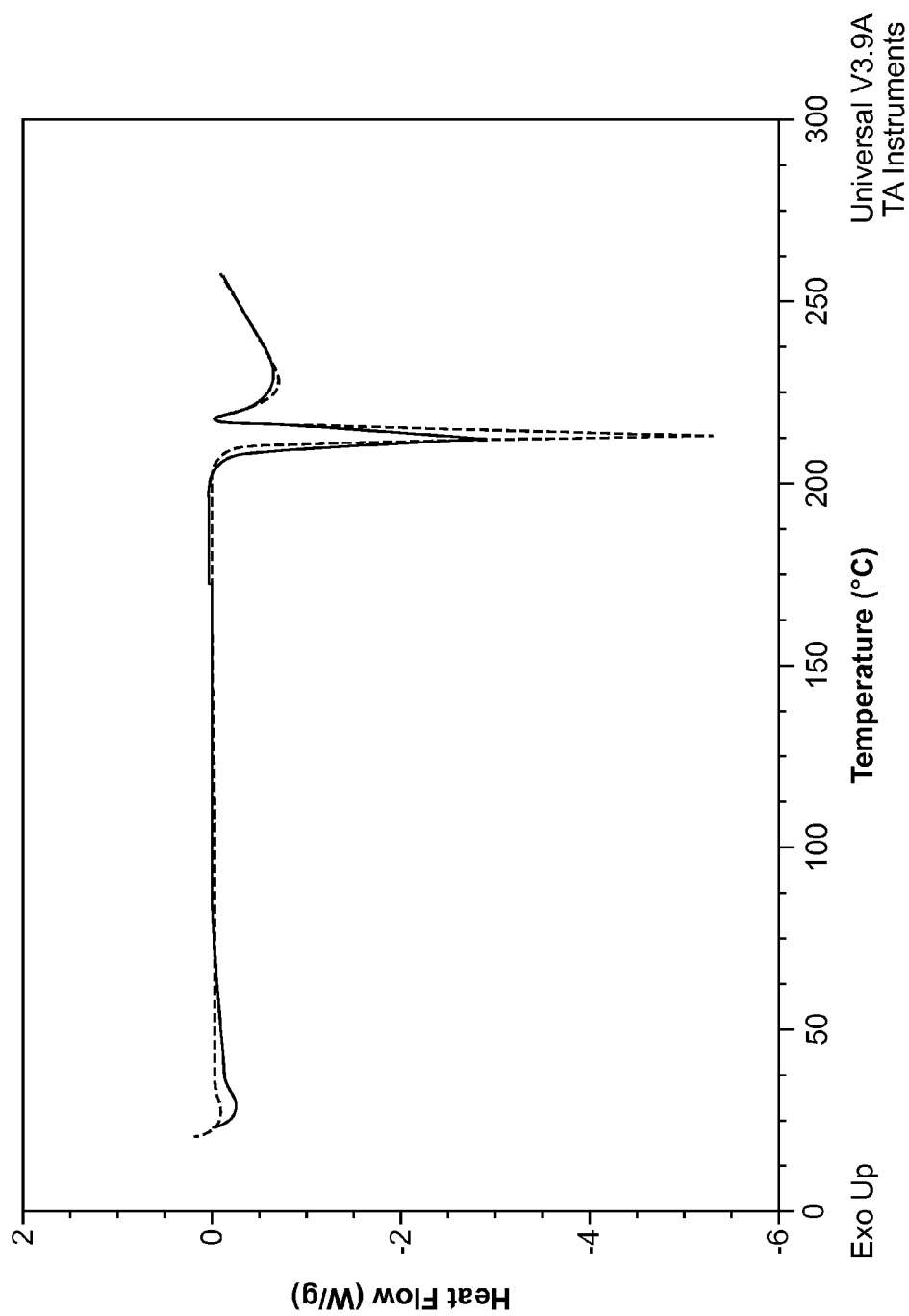
FIG. 14 provides DSC patterns of the polymorphs shown in FIG. 12, in which the DSC pattern of Form II is represented by the dashed line and the DSC pattern of Form III is represented by the solid line. This figure suggests that the hydrated water of Form III is removed readily without any noticeable endothermic event.

In some embodiments, Form II has a crystal structure characterized by a perspective view as shown in FIG. 11.

b. Form III

In another aspect, there is provided a crystalline polymorph Form III of the maleate salt of betrixaban of Formula II.

In some embodiments, Form III is characterized by properties including one or more of the following as described in details herein:
its X-ray powder diffraction pattern (XRPD);
its infrared spectrum (IR);
its differential scanning calorimetry (DSC);
its thermogravimetric analysis (TGA);
its vapor sorption curve;
solid state NMR, and
crystal structure, such as unit cell structure.

In some embodiments, Form III exhibits an X-ray powder diffraction pattern having at least the following approximate characteristic peak locations 15.1, 2.2, 4.9, 17.4, 10.0, and 22.4 degrees 2θ. In one embodiment, the X-ray powder diffraction pattern is characterized with peaks having a relative intensity of 10% or more: 15.1, 2.2, 4.9, 17.4, 10.0, 22.4, 26.5, and 2.9 degrees 2θ. In another embodiment, the X-ray powder diffraction pattern has at least six, or eight, or ten, or all of the approximate characteristic peak locations selected from 15.1, 2.2, 4.9, 17.4, 10.0, 22.4, 26.5, 2.9, 24.6, 19.4, 24.2, 16.3, 20.7, 22.9, 29.0, 9.6, 18.0, 18.5, 29.3, 22.0, and 30.3 degrees 2θ. In another embodiment, the X-ray powder diffraction pattern has at least four, six, eight, ten or all of the approximate characteristic peak locations of 15.1, 2.2, 4.9, 17.4, 10.0, 22.4, 26.5, 2.9, 24.6, 19.4, 24.2, 16.3, 20.7, 22.9, 29.0, 9.6, 18.0, 18.5, and 29.3 degrees 2θ. In yet another embodiment, the X-ray powder diffraction pattern comprises or consists of all peaks listed in Table 3.

TABLE 3

Peak Position, d-Spacing and Peak Height of Form III

| Peak Position [°2θ] | Relative Intensity [%] | FWHM [°2θ] | d-spacing [Å] | Tip width [°2θ] | Height [counts] |
|---|---|---|---|---|---|
| 15.1 | 100 | 0.1004 | 5.87 | 0.102 | 17135.6 |
| 2.2 | 82.53 | 0.184 | 39.37 | 0.187 | 14141.7 |
| 4.9 | 65.67 | 0.0669 | 17.96 | 0.068 | 11253.1 |
| 17.4 | 30.27 | 0.1506 | 5.10 | 0.153 | 5187.5 |
| 10.0 | 27.24 | 0.1004 | 8.85 | 0.102 | 4668.0 |
| 22.4 | 21.34 | 0.1004 | 3.97 | 0.102 | 3656.5 |
| 26.5 | 10.68 | 0.1673 | 3.37 | 0.17 | 1830.0 |
| 2.9 | 10.23 | 0.1004 | 30.32 | 0.102 | 1753.3 |
| 24.6 | 9.63 | 0.0836 | 3.62 | 0.085 | 1650.47 |
| 19.4 | 9.47 | 0.1004 | 4.58 | 0.102 | 1623.4 |
| 24.2 | 8.36 | 0.1338 | 3.68 | 0.136 | 1432.1 |
| 16.3 | 6.81 | 0.1004 | 5.45 | 0.102 | 1166.5 |
| 20.7 | 6.14 | 0.1171 | 4.30 | 0.119 | 1051.6 |
| 22.9 | 5.98 | 0.1004 | 3.88 | 0.102 | 1025.1 |
| 29.0 | 5.77 | 0.1004 | 3.08 | 0.102 | 988.2 |
| 9.6 | 5.21 | 0.0502 | 9.22 | 0.051 | 892.2 |
| 18.0 | 5.17 | 0.1673 | 4.93 | 0.17 | 885.4 |
| 18.5 | 5.17 | 0.1171 | 4.80 | 0.119 | 885.2 |
| 29.3 | 5.14 | 0.1506 | 3.04 | 0.153 | 880.6 |
| 22.0 | 5.06 | 0.0836 | 4.04 | 0.085 | 867.9 |
| 30.3 | 5 | 0.1004 | 2.95 | 0.102 | 857.3 |
| 23.7 | 4.94 | 0.1171 | 3.76 | 0.119 | 845.9 |
| 19.2 | 4.67 | 0.1506 | 4.63 | 0.153 | 799.6 |
| 25.2 | 4.34 | 0.0836 | 3.54 | 0.085 | 744.4 |
| 9.5 | 4.32 | 0.0502 | 9.35 | 0.051 | 740.1 |
| 22.7 | 3.89 | 0.1004 | 3.91 | 0.102 | 666.7 |
| 26.7 | 3.51 | 0.1004 | 3.33 | 0.102 | 602.3 |
| 34.5 | 3.39 | 0.1004 | 2.60 | 0.102 | 581.3 |
| 36.2 | 3.38 | 0.1673 | 2.48 | 0.17 | 578.8 |
| 14.0 | 3.28 | 0.1171 | 6.33 | 0.119 | 561.4 |
| 25.0 | 3.1 | 0.0836 | 3.57 | 0.085 | 530.6 |
| 19.8 | 3.05 | 0.1004 | 4.49 | 0.102 | 522.7 |
| 27.3 | 3.02 | 0.0502 | 3.27 | 0.051 | 517.7 |
| 32.3 | 2.9 | 0.2007 | 2.77 | 0.204 | 496.3 |

TABLE 3-continued

Peak Position, d-Spacing and Peak Height of Form III

| Peak Position [°2θ] | Relative Intensity [%] | FWHM [°2θ] | d-spacing [Å] | Tip width [°2θ] | Height [counts] |
|---|---|---|---|---|---|
| 14.4 | 2.85 | 0.0836 | 6.15 | 0.085 | 488.9 |
| 27.8 | 2.81 | 0.1171 | 3.21 | 0.119 | 480.7 |
| 21.5 | 2.74 | 0.2007 | 4.13 | 0.204 | 469.2 |
| 35.9 | 2.39 | 0.1004 | 2.50 | 0.102 | 409.2 |
| 32.7 | 2.07 | 0.2007 | 2.74 | 0.204 | 355.5 |
| 20.2 | 2.02 | 0.0836 | 4.40 | 0.085 | 346.3 |
| 6.4 | 1.97 | 0.4015 | 13.90 | 0.408 | 336.9 |
| 8.0 | 1.88 | 0.0669 | 11.00 | 0.068 | 322.3 |
| 26.0 | 1.76 | 0.1004 | 3.43 | 0.102 | 301.7 |
| 31.2 | 1.75 | 0.1338 | 2.87 | 0.136 | 299.5 |
| 16.5 | 1.57 | 0.0836 | 5.36 | 0.085 | 268.4 |
| 37.4 | 1.16 | 0.1673 | 2.40 | 0.17 | 198.5 |
| 36.8 | 1.15 | 0.1338 | 2.44 | 0.136 | 197.3 |
| 39.0 | 1.11 | 0.4015 | 2.31 | 0.408 | 189.6 |

In some embodiments, Form III is a hydrate. In some embodiments, Form III is a hemihydrate. In some embodiments, the Form III is a channel hydrate.

In some embodiments, Form III is a hemihydrate with two independent salt pairs of betrixaban and maleic acid in a crystallographic asymmetric unit. The two cations have dissimilar overall conformations arising from a substantial rotation about the N1-C11 bond of approximately 100 degrees. In some embodiments, the crystal structure is characterized by a unit cell structure with the following cell parameters at 100 K:

| | | |
|---|---|---|
| a = 8.2369(4) Å | α = 107.045(4)° | V = 2675.7(2) Å$^3$ |
| b = 18.3639(9) | β = 93.758(4) | Space group = P1, #2 |
| c = 18.5623(9) | γ = 91.459(4) | Z = 2 |

Figure 16:
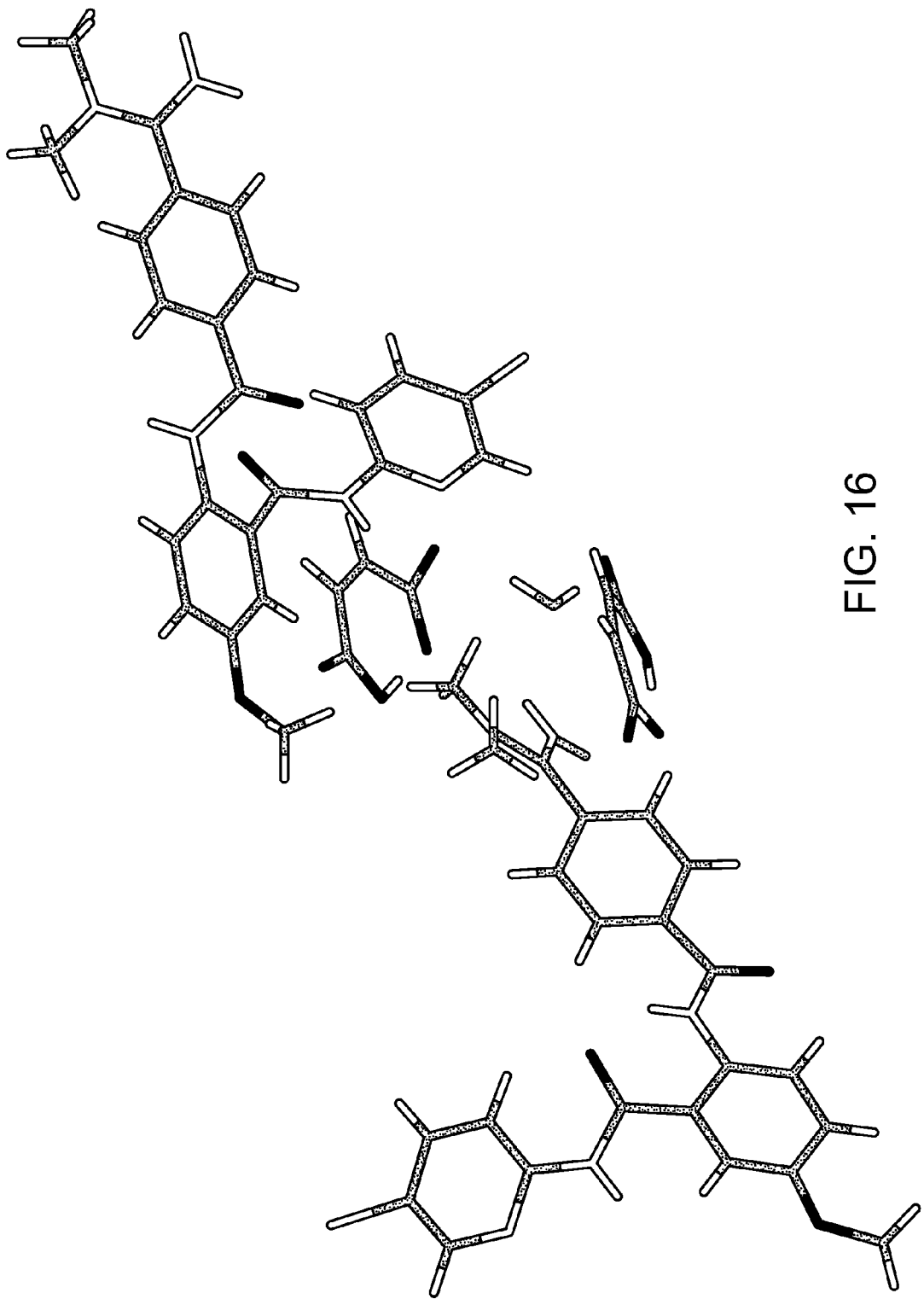
FIG. 16 provides a perspective view of Form III, which is a hemihydrate polymorph, showing two independent ion-pairs of the maleate salt associated with one water molecule.

In some embodiments, Form III has a crystal structure characterized by a perspective view as shown in FIG. 16.

Figure 20:
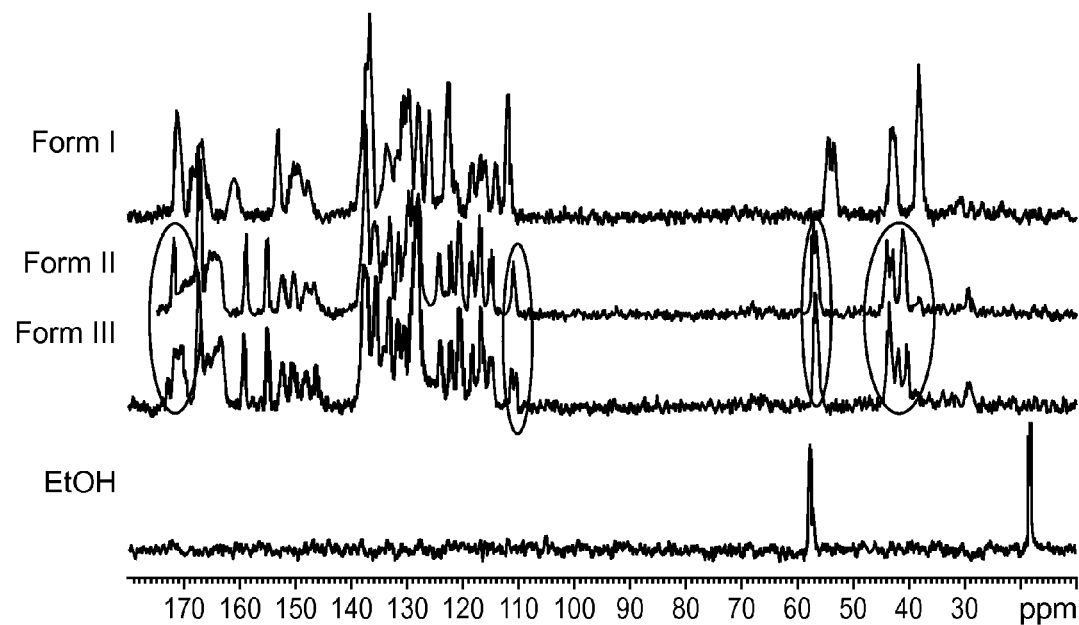
FIG. 20 provides carbon solid state NMR spectra of Form I, Form II, and Form III.
Figure 21:
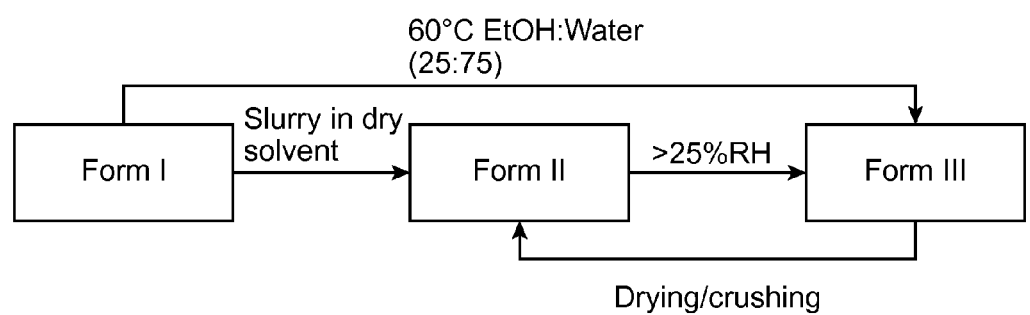
FIG. 21 provides a diagram showing conversion of Form I, Form II and Form III.

The variable relative humidity (RH) XPRD data suggest that Form II converts to a weak hemihydrate (Form III) at greater than 25% RH. The formation of the hemihydrate is also confirmed by carbon SSNMR of a sample in water. FIG. 20 shows carbon SSNMR spectra for Form I, Form II, and Form III, which displays peak shift associated with water incorporated into the lattice of Form III. The DSC trace for this hemihydrate is substantially identical to that of Form II, indicating that the water is loosely bound in the lattice of the hemihydrate.

c. Methods of Preparing Form II and Form III

In another aspect, there is provided a method for preparing the crystalline polymorphs described herein. In some embodiments, the method is for preparing Form II, which method comprises heating a composition comprising betrixaban maleate salt in a solvent to a temperature of at least about 50° C. to obtain a solution, and cooling the solution to at or below about 20° C. but above the freezing temperature of the solvent, wherein the solvent comprises an organic solvent selected from the group consisting of ethanol, tetrahydrofuran, methyl tert-butyl ether, dimethylformamide, and toluene, and combinations thereof, and optionally water. In some embodiments, the method further comprises seeding the solution with a Form II crystal.

In some embodiments, the method is for preparing Form II, which method comprises heating a composition comprising betrixaban free base and at least one equivalent of maleic acid in a solvent comprising water and optionally ethanol to a temperature of about 45° C. to about 60° C., addition of a seed crystal of Form II, and cooling the solution to at or below about 30° C. but above the freezing temperature of the solvent. In some embodiments, the solvent comprises water and ethanol in a volume ratio of about 65:35.

In some embodiments, the method further comprises collecting the crystalline form and drying the crystalline form to a water content of equal to or less than about 1% w/w, or equal to or less than about 0.5 w/w.

Form II can be prepared by dissolving the maleate salt of Formula II (which may be in Form I) in a solvent at a temperature which is above room temperature but below the boiling point of the solvent (for example about 50-70° C.), optionally followed by addition of a seed of Form II to ensure that Form II grows, and cooling the solution slowly (for example to 0° C. over 16 hours). In some embodiments, the solvent comprises an anhydrous solvent such as, e.g., dry ethanol. In some embodiments, the solvent comprises water. The ratio of the ethanol to water in the solvent may vary. In some embodiments, the ratio can be up to about 1:1 v/v. In some embodiments, the ratio is from about 1:3 to 1:1 v/v. Other solvents that can be used include tetrahydrofuran, methyl tert-butyl ether, dimethylformamide, and toluene, for example, mixtures of tetrahydrofuran/water, methyl tert-butyl ether/dimethylformamide, and toluene/dimethylformamide. Betrixaban can be prepared according to methods described in U.S. Pat. Nos. 6,376,515 and 7,598,276, and U.S. patent application Ser. No. 12/969,371, filed Dec. 15, 2010, all of which are hereby incorporated by reference in their entirety. Preparation of Form I of the Maleate Salt of Betrixaban is also Described in U.S. Pat. No. 7,598,276. Form I is favored when supersaturation is high and nucleation dominates under less-controlled process. Form II is favored when there is adequate Form II seed and the crystallization is slow enough that growth dominates over nucleation.

Form III can be prepared by recrystallizing the maleate salt in a suitable solvent in which betrixaban maleate is completely or partially soluble at a desired temperature. In some embodiments, the solvent comprises greater than 25 volume % of water. Other solvents can be used in combination with water include ethanol, tetrahydrofuran, methyl tert-butyl ether, dimethylformamide, and toluene, for example, mixtures of tetrahydrofuran/water, methyl tert-butyl ether/dimethylformamide, and toluene/dimethylformamide. In some embodiments, the solvent comprises ethanol and water in a ratio of 25:75 v/v. In some embodiments, the solvent comprises ethanol and water in a ratio of 1:9 v/v. In some embodiments, Form III is formed in such a solvent at a temperature that is higher than room temperature, for example, at about 60° C.

Hemihydrate Form III may be converted to the anhydrous polymorph Form II when it is dried and/or crushed. The anhydrous polymorph Form II may be converted to the hemihydrate Form III when it is exposed to a relative humidity of greater than 25%.

III. Pharmaceutical Compositions

The crystalline forms provided herein may be used in the preparation of pharmaceutical compositions comprising betrixaban to administer to a subject for preventing or treating the subject suffering from a condition, wherein the condition is characterized by undesired thrombosis. The pharmaceutical compositions provided herein are comprised of a pharmaceutically acceptable carrier and a therapeutically acceptable amount of betrixaban in the form of the crystalline forms provided herein or derived from the crystalline forms.

A. Pharmaceutically Acceptable Carriers

In the management of thrombotic disorders the crystalline forms provided herein may be utilized in compositions such as tablets, capsules, lozenges or elixirs for oral administration, suppositories, sterile solutions or suspensions or injectable administration, and the like, or incorporated into shaped articles. Subjects in need of treatment (typically mammalian subjects) can be administered appropriate dosages of the crystalline forms provided herein that will provide optimal efficacy. The dose and method of administration will vary from subject to subject and be dependent upon such factors as the type of mammal being treated, its sex, weight, diet, concurrent medication, overall clinical condition, the specific use for which these polymorphs are employed, and other factors which those skilled in the medical arts will recognize.

Capsules can be prepared using conventional and known encapsulation techniques, such as that described in Stroud et al., U.S. Pat. No. 5,735,105. The capsule is typically a hollow shell of generally cylindrical shape having a diameter and length sufficient so that the pharmaceutical solution compositions containing the appropriate dose of the active agent fit inside the capsule. The exterior of the capsules can include plasticizer, water, gelatin, modified starches, gums, carrageenans, and mixtures thereof. Those skilled in the art will appreciate what compositions are suitable.

In addition to the active agent, tablets can comprise fillers, binders, compression agents, lubricants, disintegrants, colorants, water, talc and other elements recognized by one of skill in the art. The tablets can be homogeneous with a single layer at the core, or have multiple layers in order to realize preferred release profiles. In some instances, the tablets may be coated, such as with an enteric coating. One of skill in the art will appreciate that other excipients are useful in the tablets.

Lozenges include an appropriate amount of the active agent as well as any fillers, binders, disintegrants, solvents, solubilizing agents, sweeteners, coloring agents and any other ingredients that one of skill in the art would appreciate is necessary or desire. Lozenges are designed to dissolve and release the active agent on contact with the mouth of the patient. One of skill in the art will appreciate that other delivery methods are useful.

Formulations of the polymorphs provided herein are prepared for storage or administration by mixing the crystalline forms with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro Ed. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium, and/or nonionic surfactants such as Tween, Pluronics or polyethyleneglycol.

In some embodiments, dosage formulations comprising the crystalline forms or made from the crystalline forms to be used for therapeutic administration is sterile. Sterile crystalline forms may be prepared by conventional methods. Sterility of the pharmaceutical composition can be readily accomplished by filtration through sterile membranes such as 0.2 micron membranes, or by other conventional methods. Formulations may be stored in lyophilized form or as an aqueous solution. The pH of the preparations typically will be between 3 and 11, more preferably from 5 to 9 and most preferably from 7 to 8. It will be understood that use of certain of the foregoing excipients, carriers, or stabilizers may result in the formation of cyclic polypeptide salts. Route of administration may be by injection, such as intravenous (bolus and/or infusion), subcutaneous, intramuscular, or by oral, colonical, rectal, nasal or intraperitoneal administration, employing a variety of dosage forms such as suppositories, implanted pellets or small cylinders, aerosols, oral dosage formulations (such as tablets, capsules and lozenges) and topical formulations such as ointments, drops and dermal patches. The compositions may be incorporated into shaped articles such as implants which may employ inert materials such as biodegradable polymers or synthetic silicones, for example, Silastic, silicone rubber or other polymers commercially available.

The crystalline forms provided herein may also be used in preparation of compositions which deliver betrixaban in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The crystalline forms provided herein may also be used in the preparation of compositions in which betrixaban is delivered by the use of antibodies, antibody fragments, growth factors, hormones, or other targeting moieties, to which the salt molecules are coupled. The crystalline forms provided herein may also be used in the preparation of compositions in which betrixaban is coupled with suitable polymers as targetable drug carriers. Such polymers can include polyvinylpyrrolidinone, pyran copolymer, polyhydroxy-propylmethacrylamide-phenol, polyhydroxyethyl-aspartamide-phenol, or polyethyleneoxide-polylysine substituted with palmitoyl residues. Furthermore, crystalline forms provided herein may be used in the preparation of compositions in which betrixaban is coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic liquid formulations generally are placed into a container having a sterile access port, for example, an intravenous solution bag or vial having a stopper pierceable by hypodermic injection needle.

Typical adjuvants which may be incorporated into tablets, capsules, lozenges and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In some embodiments, the pharmaceutical composition comprise's a pharmaceutically acceptable carrier and a polymorph provided herein, wherein the pharmaceutical composition is in a solid form or a suspension in a liquid excipient and the polymorph may provide improved thermo and hydrolytic stability, handling, flowability, and/or purity, which may provide improved pharmacokinetic profile, efficacy and/or safety profile.

In some embodiments, the pharmaceutical composition is in a liquid solution form and comprises a pharmaceutically acceptable carrier and is prepared from a polymorph provided herein. The polymorph in such a composition may provide improved thermo and hydrolytic stability, handling, purity and solubility, which may provide improved pharmacokinetic profile, efficacy and/or safety profile.

In some embodiments, the crystalline provided herein is administered orally in a composition comprising Form II or Form III, or a mixture thereof, dextrose monohydrate, croscarmellose sodium and magnesium stearate. The composition is granulated and filled into a hard gelatin capsule. In some embodiments, the oral composition is an immediate release (IR) capsule comprises 15, 20, 30, 40, 60, 80 or 90 mg of Form II or Form III, or a mixture thereof. In some embodiments, the oral composition is a delayed release enteric coated (EC) tablet comprising 15, 20, 30, 40, 60, 80 or 90 mg of Form II or Form III, or a mixture thereof. In some embodiments, the capsule or tablet comprises 20 mg, 30 mg and 40 mg of Form II or Form III, or a mixture thereof.

B. Dosing

Therapeutically effective dosages may be determined by either in vitro or in vivo methods. The optimal dosage required may be determined according to the patient's condition, age, gender, weight, etc. The range of therapeutically effective dosages will be influenced by the route of administration, the therapeutic objectives and the condition of the patient. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of the polymorphs are commenced at lower dosage levels, with dosage levels being increased until the desired effect is achieved.

Typically, about 0.5 to 500 mg of a crystalline form provided herein is combined with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

It is contemplated that a typical dosage will range from about 0.001 mg/kg to about 1000 mg/kg, preferably from about 0.01 mg/kg to about 100 mg/kg, and more preferably from about 0.10 mg/kg to about 20 mg/kg. The crystalline forms provided herein may be administered once or several times daily and other dosage regimens may also be useful. U.S. Patent Application Publication No. 2008/0153876 provides detailed betrixaban dosing information, which is hereby incorporated by reference in its entirety.

In some embodiments, the dosage is an aggregate daily dose of between 40 mg and 140 mg of betrixaban or betrixaban maleate salt (comprising Form II and/or Form III) and may be administered once, twice or three times daily. In some embodiments, the dosage is an aggregate daily dose of between 40 mg and 120 mg and may be administered once, twice or three times daily. In some embodiments, the dosage is an aggregate daily dose of 40, 50, 60, 70, 80, 90, 100, 110 or 120 mg and may be administered once, twice or three times daily, preferably once or twice daily. In some embodiments, the dosage is an aggregate daily dose of 40, 60 or 80 mg and may be administered once or twice daily, preferably once daily.

IV. Methods

A. Preventing and Treating Disease Conditions Characterized by Undesired Thrombosis The crystalline forms provided herein can be used for preventing or treating a condition characterized by undesired thrombosis in a mammal by administering to the mammal a therapeutically effective amount of a crystalline form of the maleate salt of betrixaban. The polymorphs can be used either alone or in conjunction with pharmaceutically acceptable excipients to prevent the onset of a condition characterized by undesired thrombosis. Prophylactic treatment can have substantial benefits for a patient at risk of an ailment, through decreased medical treatments and their associated mental and physical costs, as well as the direct monetary savings from avoiding prolonged treatment of a patient. For patients where the condition is not detected sufficiently early to prevent onset, the polymorphs provided herein can be used either alone or in conjunction with pharmaceutically acceptable excipients to treat the condition.

The crystalline forms provided herein are characterized by their ability to inhibit thrombus formation with acceptable effects on classical measures of coagulation parameters, platelets and platelet function, and acceptable levels of bleeding complications associated with their use while exhibiting suitable stability. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The crystalline forms provided herein are believed to be useful for preventing or treating a condition characterized by undesired thrombosis, such as (a) the treatment of any thrombotically mediated acute coronary syndrome including myocardial infarction, unstable angina, refractory angina, occlusive coronary thrombus occurring post-thrombolytic therapy or post-coronary angioplasty, (b) the treatment of any thrombotically mediated cerebrovascular syndrome including embolic stroke, thrombotic stroke or transient ischemic attacks, (c) the treatment of any thrombotic syndrome occurring in the venous system including deep venous thrombosis or pulmonary embolus occurring either spontaneously or in the setting of malignancy, surgery or trauma, (d) the treatment of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment of thrombotic complications associated with extracorporeal circulation (e.g. renal dialysis, cardiopulmonary bypass or other oxygenation procedure, plasmapheresis), (f) the treatment of thrombotic complications associated with instrumentation (e.g. cardiac or other intravascular catheterization, intra-aortic balloon pump, coronary stent or cardiac valve), and (g) those involved with the fitting of prosthetic devices.

In one embodiment, provided is a method for treating a condition characterized by undesired thrombosis in a mammal which comprises administering to the mammal a therapeutically effective amount of a crystalline form provided herein. Disease states that are contemplated to be treatable using the crystalline forms provided herein include, but are not limited to, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, thromboembolic stroke, systemic embolism, ischemic stroke, venous thromboembolism, atrial fibrillation, non-valvular atrial fibrillation, atrial flutter, transient ischemic attacks, venous thrombosis, deep venous thrombosis, pulmonary embolus, coagulopathy, disseminated intravascular coagulation, thrombotic thrombocytopenic purpura, thromboanglitis obliterans, thrombotic disease associated with heparin-induced thrombocytopenia, thrombotic complications associated with extracorporeal circulation, thrombotic complications associated with instrumentation, thrombotic complications associated with the fitting of prosthetic devices, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

In some embodiments, the polymorphs provided herein are useful in:
  prevention of stroke in atrial fibrillation patients (Stroke Prevention in Atrial Fibrillation (SPAF));
  prevention of thrombosis in medically ill patients, such as acute medically ill patients;
  prevention and treatment of deep vein thrombosis;
  prevention and treatment of thrombosis in patients with hip or knee surgery;
  prevention of arterial thrombosis in acute coronary syndrome patients; and/or
  secondary prevention of acute coronary syndrome, myocardial infarction, stroke or other thrombotic events in patients who have had a prior event (e.g., including but not limited to a myocardial infarction or stroke event).

In some embodiments, the condition is selected from the group consisting of embolic stroke, thrombotic stroke, venous thrombosis, deep venous thrombosis, acute coronary syndrome, and myocardial infarction.

In some embodiments, the methods are useful in treating thromboembolic stroke, ischemic or hemorrhagic stroke, systemic embolism, non-valvular atrial fibrilaiton, venous thromboembolism (VTE), stroke prevention in atrial fibrillation (SPAF), prevention of VTE in knee or hip surgery, prevention of VTE in acute medically ill patients, and secondary prevention in acute coronary syndrome (ACS).

In some embodiments, the polymorphs provided herein are useful in: prevention of stroke in atrial fibrillation patients; prevention of thrombosis in medically ill patients; prevention and treatment of deep vein thrombosis; prevention of arterial thrombosis in acute coronary syndrome patients; and/or secondary prevention of myocardial infarction, stroke or other thrombotic events in patients who have had a prior event.

The polymorphs provided herein can also be used whenever inhibition of blood coagulation is required such as to prevent coagulation of stored whole blood and to prevent coagulation in other biological samples for testing or storage. Thus the crystalline forms provided herein can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prosthesis, cardiac prosthesis, and extracorporeal circulation systems.

Besides being useful for human treatment, these polymorphs are also contemplated to be useful for veterinary treatment of companion animals, exotic animals and farm animals, including mammals, rodents, and the like. More preferred animals include horses, dogs, and cats.

B. Combination Therapies

The crystalline forms provided herein may also be used in combination with other therapeutic or diagnostic agents. In certain preferred embodiments, the crystalline forms provided herein may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin.

In some embodiments, the polymorph forms provided herein are coadministered with a second therapeutic agent selected from the group consisting of a thrombin inhibitor, a thrombolytic agent, an antiarrhythmic agent, a cholesterol or triglyceride agent, or combinations thereof.

In some embodiments, the second therapeutic agent is selected from the group consisting of a GP IIb/IIIa receptor antagonist, a P2Y12 receptor antagonist, a phosphodiesterase III inhibitor, a thromboxane synthase inhibitor, a thromboxane A2 receptor antagonist, a thrombin receptor antagonist, and an inhibitor of p selectin.

In some embodiments, the second therapeutic agent is selected from the group consisting of: abciximab, eptifibatide, tirofiban, acetylsalicylic acid, cangrelor, ticagrelor, clopidogrel, ticlopidine, prasugrel, dipyridamole, aggrenox, SCH530348, PSI-697, ifetroban, cilostazol, isbogrel, furegrelate, ramatroban, ridogrel, terbogrel, Servier S 18886 and ozagrel.

In some embodiments, the second therapeutic agent is eptifibatide or clopidogrel.

In some embodiments, the second therapeutic agent is a platelet ADP receptor inhibitor. In some embodiments, the second therapeutic agent is a specific antagonist of $P2Y_{12}$. In some embodiments, the second therapeutic agent is elinogrel, having the name N-[(5-chlorothiophen-2-yl)sulfonyl]-N'-{4-[6-fluoro-7-(methylamino)-2,4-dioxo-1,4-dihydroquinazolin-3(2H)-yl]phenyl}urea or [4-(6-fluoro-7-methylamino-2,4-dioxo-1,4-dihydro-2H-quinazolin-3-yl)-phenyl]-5-chloro-thiophen-2-yl-sulfonylurea and is of the formula:

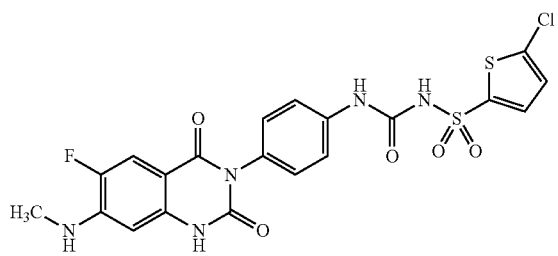 [SMILES: CNc1cc2[nH]c(=O)n(-c3ccc(NC(=O)NS(=O)(=O)c4ccc(Cl)s4)cc3)c(=O)c2cc1F]

or pharmaceutically acceptable salt thereof, for example, a potassium salt or a sodium salt.

In some embodiments, the second therapeutic agent is selected from the group consisting of specific inhibitors of thrombin, factor IXa, factor XIa, factor XIIa or factor VIIa, synthetic pentasaccharides, low molecular weight heparin, anti-tissue factor antibody and combinations thereof.

In some embodiments, the second therapeutic agent is an injectable anticoagulant agent.

In some embodiments, the second therapeutic agent is selected from the group consisting of bivalirudin, dabigatran, argatroban, lepirudin, warfarin, and phenocoumarol.

In some embodiments, the second therapeutic agent is selected from the group consisting of fondaparinux, danaparoid, enoxaparin, dalteparin and unfractionated heparin.

In some embodiments, the second therapeutic agent is selected from the group consisting of non-steroidal anti-inflammatory agents, tumor necrosis factor antagonists, interleukin 1 receptor antagonists, cyclooxygenase-2 inhibitors and rheumatoid arthritis agents.

In some embodiments, the second therapeutic agent is selected from the group consisting of acetylsalicylic acid, piroxicam, indomethacin, mesalamine, sulfasalazine, methotrexate, leflunomide, etanercept, infliximab, adalimubab, and anakinra.

In some embodiments, the second therapeutic agent is selected from the group consisting of diuretics, beta blockers, angiotensin converting enzyme inhibitors, angiotensin 2 receptor antagonists, and calcium channel blockers.

In some embodiments, at least one of the therapeutic agents is administered in a sub-therapeutic dosage. In some embodiments, both of the therapeutic agents are administered in sub-therapeutic dosages.

In some embodiments, the two therapeutic agents are administered simultaneously or sequentially.

The crystalline forms provided herein may act in a synergistic fashion to prevent reocclusion following a successful thrombolytic therapy and/or reduce the time to reperfusion. The crystalline forms may also allow for reduced doses of the thrombolytic agents to be used and therefore minimize potential hemorrhagic side-effects. The polymorphs provided herein can be utilized in vivo, ordinarily in mammals such as primates, humans, sheep, horses, cattle, pigs, dogs, cats, rats and mice, or in vitro. U.S. Patent Application Publication Nos. 2008/0254036 and 2008/0279845 describe combination therapies comprising betrixaban and methods thereof, which are hereby incorporated by reference in their entirety.

C. Compound Preparation

Representative methods for preparing betrixaban or a maleate salt thereof are disclosed in U.S. Pat. No. 6,844,367B1, see Example 266, U.S. Pat. No. 7,598,276 B2, U.S. Patent Application Publication US 2010/0197929 and U.S. patent application Ser. No. 12/969,371, titled "Methods of Synthesizing Factor Xa Inhibitors" and filed on Dec. 15, 2010, all of which are hereby incorporated by reference.

In another aspect, there is provided a method of preparing betrixaban comprising reacting Compound C:

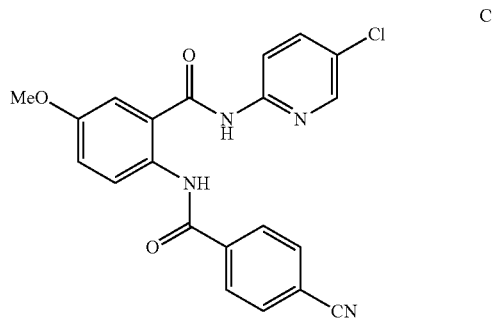 [SMILES: COc1ccc(NC(=O)c2ccc(C#N)cc2)c(C(=O)Nc2ccc(Cl)cn2)c1]

with dimethylamide lithium ($LiN(CH_3)_2$) under reaction conditions wherein the dimethylamide lithium is added over a period of not less than 3 hours at a temperature of between about 8° C. and about 12° C.

In some embodiments, the dimethylamide lithium is prepared by reacting dimethylamine ($NH(CH_3)_2$) and hexyllithium ($LiC_6H_{13}$), wherein the amount of dimethylamine is less than one equivalent of hexyllithium and optionally is less than 5 equivalents of Compound C, the amount of hexyllithium is more than 4.5 equivalents of Compound C.

In some embodiments, dimethylamine is from 4.5 equivalents to 4.9 equivalents, for example, about 4.7 equivalents, of Compound C. In some embodiments, hexyllithium is from 5 equivalents to 5.1 equivalents, for example, about 5.05 equivalents, of Compound C.

In some embodiments, the method provides betrixaban with a purity of greater than about 99%.

EXAMPLES

The materials in the examples are generally known, which may be prepared by conventional means or available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Unless stated otherwise, the abbreviations used throughout the specification have the following meanings:

Å=Angstrom
A %=total percent area
aq.=aqueous
AUC=area under curve cm=centimeter
cts=counts
d=doublet
DMF=dimethyl formamide
DMSO=dimethyl sulfoxide
DSC=differential scanning calorimetry
EDTA=ethylenediaminetetraacetic acid
eq. equivalent
EtOH=ethanol
FWHM=full width at half maximum
g=gram
HPLC=high performance liquid chromatography
hr=hour
Hz=Hertz
IPA=isopropyl alcohol
IR=infrared
J=coupling constant
KBr=potassium bromide
kg=kilogram
kV=killivolts
L=liter
LOD=limit of detection
M=molar
m=multiplet
mA=milliampere
Me=methyl
MeO=methoxy
MeOH=methanol
mg=milligram
min.=minute
mL=milliliter
mm=millimeter
MTBE=methyl tert-butyl ether
N=normal
nM=nanomolar
NMR=nuclear magnetic resonance
RH=relative humidity
s=singlet
TDS=total dissolved solids
TGA=thermal gravimetric analysis
THF=tetrahydrofuran
v/v=volume/volume
wt %=weight percent
w/w=weight/weight
w/v=weight/volume
μM=micromolar
°2θ=degree 2-theta
° C.=degree Celsius Example 1

Preparation of Form II

Form II was unexpectedly formed during preparation of Form I in two experiments using the following procedure: The maleate salt was prepared by the reaction of betrixaban with maleic acid (2.0 eq. of betrixaban) in ethanol/water (3.9:1 v/v). The solution of the resulting maleate salt was filtered and concentrated under vacuum until a final volume of 5.7 times of the weight of v/w. Water (2×v/w) was then added and the mixture back concentrated until a final volume of 5.7 v/w. The procedure of adding water and concentration until a final volume of 5.7 v/w was carried out until the molar ratio between the content of ethanol and the content of the maleate salt in the mixture was lower than, or equal to, 6. The maleate salt crystallized during the removal of the ethanol. The temperature of the suspension of the maleate salt was cooled to 19° C./25° C. and stirred for not less than 2 hours at this temperature range. The maleate salt was isolated by filtration, washed with water and dried under vacuum at a maximum temperature of 40° C. until the content of water was lower than, or equal to, 0.5% w/w by Karl-Fischer.

Experiment 1: scale 4.0 g, molar yield 92.3%, purity 98.9%, light yellow, $T_{onset}$ of endotherm detected in DSC 216.28° C.

Experiment 2: scale 5.0 g, molar yield 89.6%, purity 98.8%, off-white, $T_{onset}$ of endotherm detected in DSC 196.98° C.

A X-ray diffraction pattern for Form II obtained from Experiments 1 and 2 is shown in FIG. 2. An infrared spectrum of Form II is presented in FIG. 5A.

$^1$H NMR (DMSO-$d_6$): δ 3.0 (s, 3H), 3.2 (s, 3H), 3.82 (s, 3H), 7.2 (d, 1H, J=9.0 Hz), 7.42 (s, 1H), 7.68 (d, 1H, J=8.0 Hz), 7.95-8.15 (m, 2H), 8.12 (m), 8.18 (m, 1H), 8.42 (s, 1H), 9.0 (s, 1H), 11.0 (s, 1H), 11.2 (s, 1H); IR (KBr, cm$^{-1}$): 3300, 1685, 1600, 1515, 1380, 1270, 1200, 1100, 1050, 880, 800, 710.

Example 2

Preparation of Form II 1.98 g of betrixaban maleate Form I was added to 24 mL of ethanol/water (25/75 ethanol/water by volume) and heated to 58° C. until it dissolved. Form II was added as seed and the mixture was allowed to cool from 58° C. to 0° C. over 16 hours to form Form II.

Physical properties are provided in the table below and elsewhere herein.

| Differential Scanning Calorimetry | Optical Microscopy | Thermo-gravimetric Analysis | Hygroscopicity |
|---|---|---|---|
| Endotherm at: Tonset = 212° C. Tpeak = 213° C. ΔH = 91 J/g Sample decomposed after melting | Anisotropic Primary particles Blade shaped crystals | 0.2% weight loss upto 195° C. | Sample adsorbed about 1 wt % water up to 95% RH. Sample placed in a 90% RH chamber for 2 weeks exhibited the same XRPD pattern as the original sample. |

The polymorph prepared above was in white blades. An X-ray diffraction pattern as determined using single crystal X-ray diffraction is provided in FIG. 3 and is characterized by the approximate peaks in Table 1.

Example 3

Analytical Methods

X-Ray Powder Diffraction

X-Ray Powder Diffraction pattern (FIG. 3) was obtained using the following parameters: scan range)(°): 2-40; step size)(°): 0.01671; scan speed (o/s): 0.2387; total time of analysis (min:s): 2:51.

X-Ray Powder Diffraction patterns can also be collected on a Siemens D5000 diffractometer using CuKα radiation (40 kV, 40 mA), θ-θ goniometer, automatic divergence and receiving slits, a graphite secondary monochromator and a scintillation counter. The instrument is performance checked using a certified Corundum standard (NIST 1976).

Samples run under ambient conditions can be prepared as flat plate specimens using powder. Approximately 35 mg of the sample is gently packed into a cavity cut into polished, zero-background (510) silicon wafer. The sample is rotated in its own plane during analysis.

Diffraction data can be reported using Cu K$\alpha_1$ ($\lambda$=1.5406 Å), after the K$\alpha_2$ component has been stripped using EVA (evaluation software), the powder patterns can be indexed by the ITO method using WIN-INDEX and the raw lattice constants refined using WIN-METRIC.

Single Crystal X-Ray Diffraction

Data can be collected on a 1K SMART CCD diffractometer by Bruker AXS, Madison, Wis., USA, equipped with an Oxford Cryosystems Cryostream cooling device by Oxford Cryosystems Ltd.; UK. Structures can be solved using either the SHELXS or SHELXD programs and refined with the SHELXL program as part of the Bruker AXS SHELXTL suite. Unless otherwise stated, hydrogen atoms attached to carbon are placed geometrically and allowed to refine with a riding isotropic displacement parameter. Hydrogen atoms attached to a heteroatom are located in a different Fourier synthesis and are allowed to refine freely with an isotropic displacement parameter.

Crystal Data

Experiments can be performed on a Bruker-Nonius Kappa CCD diffractometer equipped with an Oxford Cryosystems Cryostream cooling device. Structures are usually solved with either SIR-97 or SHELXS-97 and refined with SHELXL-97. Hydrogen atoms can be placed geometrically and allowed to refine with isotropic displacement parameters.

Optical Microscopy

Sample was dispersed in mineral oil onto glass slide, covered with a cover glass and observed under cross-polarizers at 10× magnification to obtain optical micrograph FIG. 1.

Differential Scanning calorimetry (DSC)

Differential scanning calorimetry curve (FIG. 6) was obtained under nitrogen flow at a heating rate of 10° C./min in an open aluminium pan. FIG. 6 shows one endotherm with $T_{onset}$=212° C., $T_{peak}$=213° C., and $\Delta H$=91 J/g. Sample decomposed after melting.

DSC data can also be collected on a TA instrument Q1000 by TA instrument, New Castle, Del., USA, equipped with a 50 position autosampler. The energy and temperature calibration standard was indium. Samples are heated at a rate of 10° C./min between 25 and 350° C. A nitrogen purge at 30 mL/min is maintained over the sample. Between 1 and 3 mg of sample is used, unless otherwise stated, and all samples are crimped in a hermetically sealed aluminium pan.

Thermogravimetric Analysis (TGA)

Thermogravimetric-analysis curve (FIG. 7) was obtained under a nitrogen flow at a heating rate of 10° C./min.

TGA data can be collected on a TA Instrument Q500 TGA, calibrated with Nickel/Alumel and running at scan rates of 10° C./minute. A nitrogen purge at 60 mL/min is maintained over the sample. Typically 10-20 mg of sample is loaded onto a pre-tared platinum crucible.

Hygroscopicity Vapour Sorption

Hygroscopicity vapor sorption analysis was performed isothermally at 25° C. with steps of 5% RH, including a drying step at 40° C. Adsorption was performed from 5% RH to 95% RH and desorption from 95% RH to 5% RH. As shown in FIG. 15, Form II exhibited a 1% water gain up to 95% RH. The polymorph of the '276 patent exhibited a 0.07% water gain up to 95% RH.

LogP Determination

This can be done by potentiometric titration on a Sirius GlpKa instrument by Sirius Analytical Ltd., UK using three ratios of Octanol:ISA water to generate Log P, Log $P_{ion}$, and Log D values. The data can be refined using Refinement Pro software version 1.0. Predictions of LogP can be made using ACD Ver. 8.08 and Syracuse KNOW WIN Ver. 1.67 software.

Solubility

Sample was slurried in the solvent for 24 hours at 25° C. Solids were checked by XRPD and the liquid was submitted for quantification by HPLC. Results are in the table below.

|  | Solubility at 25° C. | |
| --- | --- | --- |
| Solvent | Form I | Form II |
| Anhydrous ethanol (0.03% water) | 5.22 | 4.8 |
| Water | 2.7 | 2.4 |
| IPA | 0.81 | 0.63 |
| MeOH* | 34.8 (yellow solvate) | 37.9 (yellow solvate) |
| MTBE | 0.001 | 0.01 |
| DMF | 275.5 | >246 |
| Acetone | 0.91 | 0.99 |
| 11.7% w/w water in EtOH (10% v/v) | 23.85 | |
| 22.4% w/w water in EtOH (20% v/v) | 50.18 | |
| EtOH/H$_2$O (25/75% w/w) | | 48.42 |

*A dichloromethane solvate has also been produced.

Solubility can also be measured by suspending enough salt in 0.25 mL of solvent (water) to give a maximum final concentration of ≥10 mg/mL of the parent free form of the salt. The suspension is equilibrated at 25° C. for 24 hr followed by a pH check and filtration through a glass fibre C 96 well plate. The filtrate is then diluted down 101 times. Quantitation is by HPLC with reference to a standard dissolved in DMSO at approx 0.1 mg/mL. Different volumes of the standard, diluted and undiluted tests are injected. The solubility is calculated by integration of the peak area found at the same retention time as the peak maximum in the standard injection. If there is sufficient solid in the filter plate the XRPD can be checked for phase changes, hydrate formation, amorphization, crystallization, etc.

pKa Determination

This can be performed on a Sirius GlpKa instrument with a D-PAS attachment. Measurements can be made by UV in aqueous and by potentiometric in methanol and water mixtures at 25° C. The titration media is ionic strength adjusted with 0.15 M KCl. The values found in the methanol and water mixtures are corrected to 0% co-solvent via a Yasuda-Shedlovsky extrapolation. The data can be refined using Refinement Pro software version 1.0. Prediction of pKa values can be made using ACD pKa prediction software Ver. 8.08.

Karl Fisher Water Determination

Water contents can be measured on a Mettler Toledo DL39 Coulometer by Mettler-Toledo Inc., Columbus, Ohio, USA using Hydranal Coulomat AG reagent and an Argon purge. Samples are introduced into the vessel as solids weighed out onto a platinum TGA pan which is connected to a subaseal to avoid water ingress. Approximately 10 mg of sample can be used per titration and each analysis is performed in duplicate.

Selected Characteristics of Betrixaban Maleate Form I and Form II

|  | Betrixaban Maleate Form I | Betrixaban Maleate Form II |
| --- | --- | --- |
| Physical Appearance | White to yellow crystalline solid | White to pale yellow crystalline solid |
| Melting Point | 200-202° C. | 212° C. |

-continued

|  | Betrixaban Maleate Form I | Betrixaban Maleate Form II |
| --- | --- | --- |
| Solubility at 25° C. | 2.7 mg/mL in water 5.2 mg/mL in ethanol | 2.5 mg/mL in water 4.8 mg/mL in ethanol |
| pH of saturated solution |  | 5.2-5.3 |
| pKa |  | 11.45 (amidine) |
| Hygroscopicity | Low (0.1% wt increase up to 95% RH) | Moderate (1% wt increase up to 95% RH) |

Example 4

The X-Ray crystallographic analysis of Form II was done at 100K to limit thermal motion and dynamic disorder as well as to improve the diffraction measurements. Data were collected on an Oxford Diffraction CCD diffractometer using Cu Kα radiation and integrated to a resolution of 0.84 Å$^{-1}$ which yielded 9338 unique reflections from 29684 measured reflections.

The structure was solved using direct methods. The refined model has all non-H atoms refined anisotropically, and H atoms at their calculated positions, with agreement statistics of: R1=3.5%, for 723 variables and 8044 reflections and wR2=9.5% using all 9338 reflections. A unit cell contains two independent salt pairs wherein the imine N is protonated and forms an ionic H-bond to the maleic acid counter-ion. A perspective view is provided in FIG. 11. The refinement is complete at a good level (R=3.47%) and the molecular geometry shows no unusual quantities.

A unit cell contains two independent salt pairs of betrixaban and maleic acid. The imine N(N2) is protonated and forms an ionic H-bond to the maleate moiety (2.84° A). In addition to this bond there are a number of other hydrogen-bonding interactions resulting in a complex network throughout the lattice. The crystal does not appear to be a hydrate.

Cell parameters at 100K and 273K are:

| Temp | a | b | c | α | β | γ | V, Å$^3$ |
| --- | --- | --- | --- | --- | --- | --- | --- |
| 100 | 8.284 | 18.082 | 18.681 | 71.22 | 86.76 | 89.69 | 2645 |
| 273 | 8.419 | 18.113 | 18.73 | 71.14 | 86.71 | 89.31 | 2699 |

At 100K:

| a = 8.2845(3) Å | α = 71.222(3)° | V = 2645.04(17) Å$^3$ |
| --- | --- | --- |
| b = 18.0823(8) | β = 86.759(3) | Space group = P1, #2 |
| c = 18.6811(6) | γ = 89.693(3) | Z = 4 |

Example 5

The structure of the hemihydrate was determined by single-crystal X-ray crystallography on an isolated crystal. The crystal selected was representative of the bulk sample prepared by the following procedure: A Form II material was brought completely into solution at 2.5 mg/mL with a 9:1 mixture of water and ethanol and gently heated to 50° C. for 30 minutes. The solution was then filtered while warm though a 0.45 micron syringe filter and allowed to slowly evaporate over 2 weeks. Crystals were isolated from the mother liquor and rapidly transferred to the instrument for analysis to avoid possible loss of water upon ambient drying.

Crystal data at 100K:

| a = 8.2369(4) Å | α = 107.045(4)° | V = 2675.7(2) Å3 |
| --- | --- | --- |
| b = 18.3639(9) Å | β = 93.758(4)° | Space group = P1, #2 |
| c = 18.5623(9) Å | γ = 91.459(4)° | Z = 2 |

Data were collected on a Oxford Diffraction CCD diffractometer using molybdenum Kα radiation and integrated to a resolution of 0.78 Å-1 which yielded 11788 unique reflections from 23411 measured reflections.

The structure was solved using direct methods. The refined model has all non-H atoms refined anisotropically, and H atoms at their calculated positions, with agreement statistics of: R1=4.0%, for 738 variables and 7711 reflections and wR2=8.2% using all 11788 reflections. The compound has crystallized as a hemihydrate with two independent molecules of the salt pair in the crystallographic asymmetric unit. The two cations have dissimilar overall conformations arising from a substantial rotation about the N1-C11 bond of approximately 100 degrees. A perspective view calculated from the crystallographic coordinates is presented in FIG. 16.

Example 6

The RHXRPD study was initiated with the wet hydrate form generated in pure water at 60° C. The RH study was run starting at 95% RH to 5% RH then back up to 95% RH. The XRPD could not be analyzed from 95% to 55% RH since the XRPD did not register any reflections due to the high water content of the sample.

Figure 17:
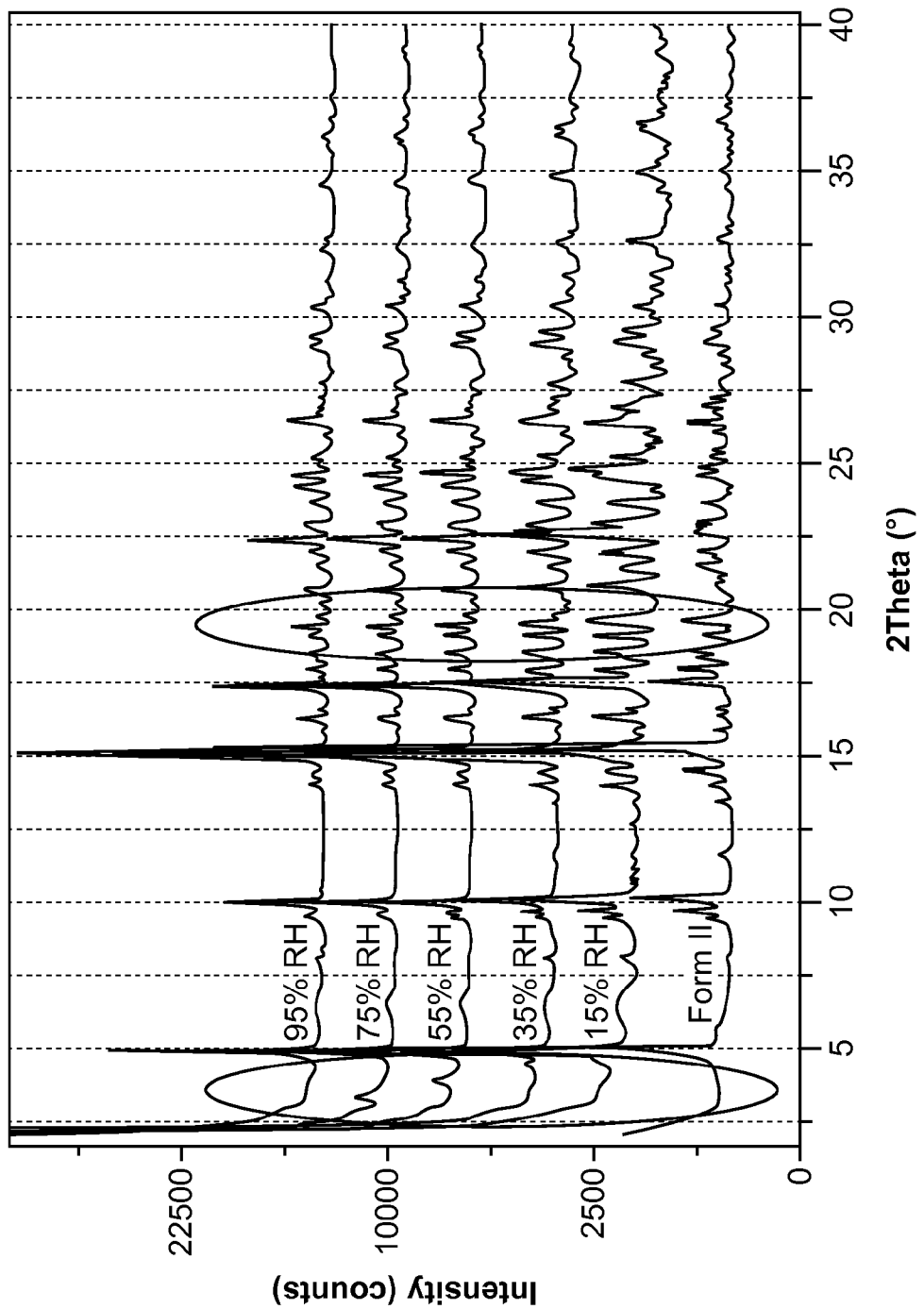
FIG. 17 provides XRPD patterns highlighting indicators of shift from Form II to Form III in the Variable Relative Humidity XRPD experiment.
Figure 18:
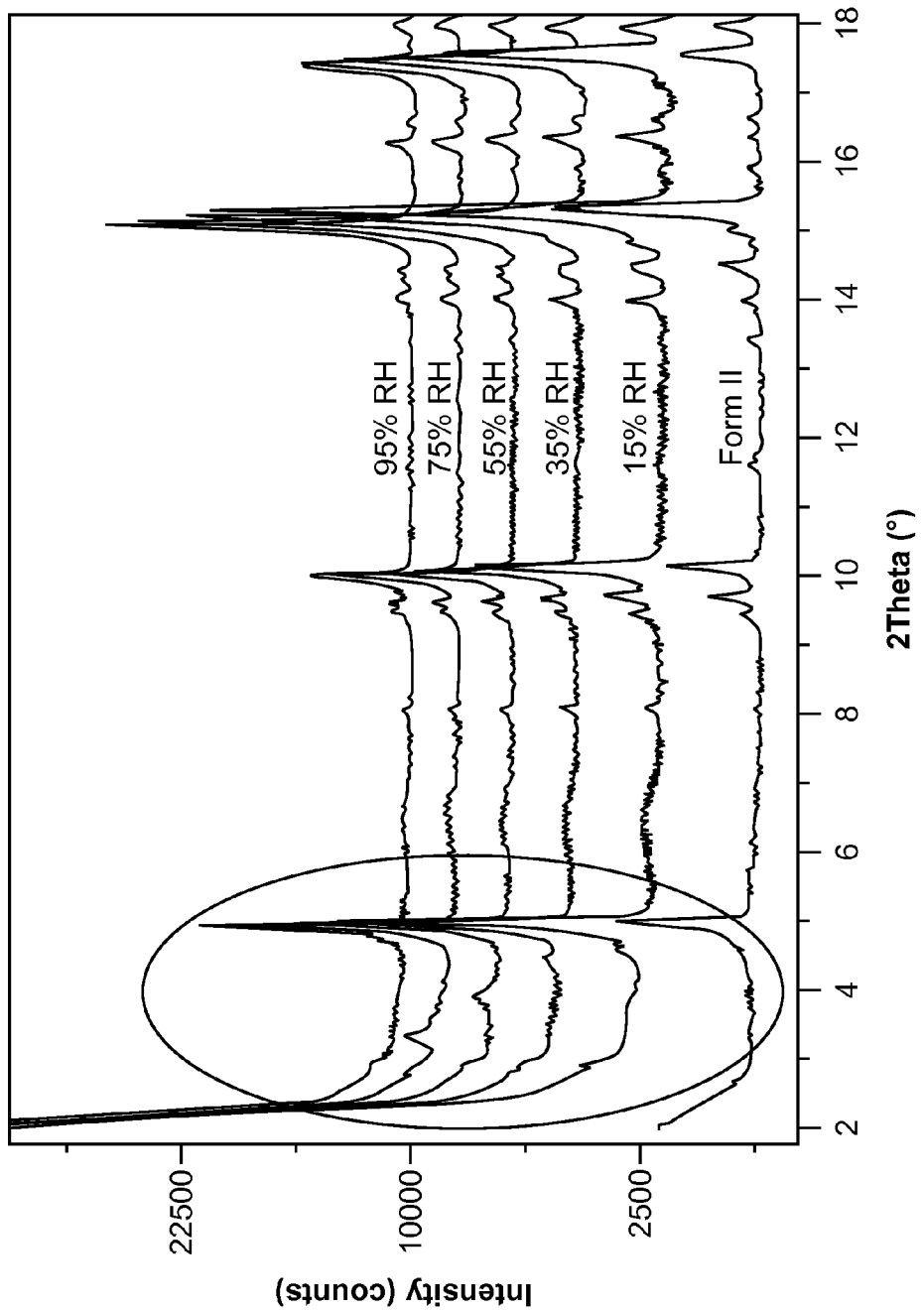
FIG. 18 provides an expanded view of a first region of the XRPD patterns of FIG. 17.
Figure 19:
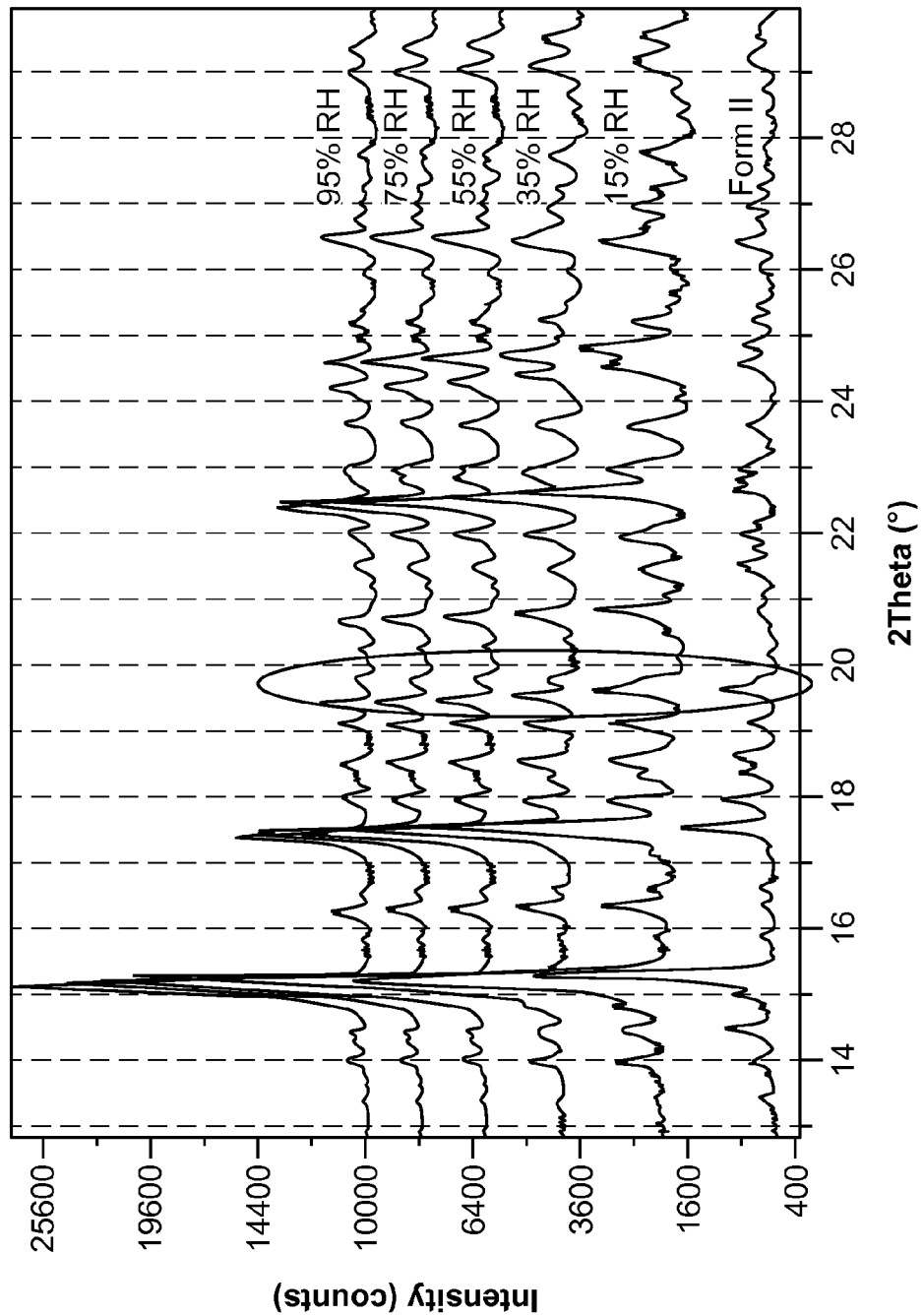
FIG. 19 provides an expanded view of a second region of the XRPD patterns of FIG. 17.

Results indicate that an additional peak starts forming to the left of the peak at 2-Theta=5 and as the RH increases the peak moves back towards 2-Theta=2. This peak is masked at 85-95% RH by interference at low diffraction angles (ref FIG. 17). Additional peak changes are observed at other regions of the XRPD spectra as seen in FIG. 18.

Other analytical methods that can be used to characterize the polymorphs provided herein are generally known in the art.

Example 7

Betrixaban freebase is dissolved in ethanol/water (35:65 v/v) at 45-60° C. with maleic acid (0.99 eq.-1.10 eq.), filtered to remove physical matter, then cooled to 45-50° C. Seed crystals of Form II maleate salt is added (0.01-0.05 eq.), and the suspension aged and cooled to <30° C. The crystals in the suspension are wet milled to reduce size, heated to 40-45° C., and re-cooled to <25° C. Form II is isolated by filtration, washed with water and dried under vacuum at maximum temperature of 40° C. until the content of water is lower than, or equal to 0.5% w/w by the Karl Fischer ("KF") technique.

Materials:

| Material | Density | Purity | Charge Amount | Moles | Eq/vol |
| --- | --- | --- | --- | --- | --- |
| Crude Freebase |  | ~98% | 300 kg | 651 | 1 eq |
| Maleic Acid |  | ~99% | 78 kg | 670 | 1.03 eq |
| Ethanol | 0.8 |  | 1400 L |  | 4.5 L/kg crude |
| Water | 1 |  | 2822 L (+750 L cakewash) |  | 8.8 L/kg crude (~2.5 L wash/ kg product) |
| Form II Seed |  | 100% | 6 kg | 10 | 0.02 eq |

Crude betrixaban freebase (300 kg) and maleic acid (78 kg) are charged to a vessel. Ethanol (1267 L) and water (2506 L) are added (for a solvent ratio of 35/65 v/v EtOH/water) and the mixture is heated to 55° C. to dissolve fully. The mixture any remain slightly turbid due to insoluble impurity.

Cyclization impurity slowly forms at elevated temperature, which can reduce yield if age time is extended. (about 3% degradation after a 24 hour age at 55° C.). This impurity is very well rejected, so purity concern is minimal (even with a 3 day 55° C. age, cyclization degradate is still fully rejected).

This solution is filtered at 55° C. to remove insoluble impurities. After combination with a line/filter flush (189 L of 35/65 EtOH/water) the solution is then cooled to 48° C. (range: 47-49° C.). Form II seed is added (6 kg, 2 wt %; can be added as solid or slurry) to induce crystallization and the batch is aged for 30 min, then cooled linearly to 20° C. over 10 hours. If seed slurry in EtOH/water is used (e.g., 90 g/L slurry from another crystallization batch) then the EtOH and water charged to dissolve the batch can be reduced by an amount equal to the solvent in the seed slurry. The batch is wetmilled (via IKA® (North Carolina) wetmill, IKA® dispersion mill, or similar) ~10-30 turnovers) and then annealed by heating to 43° C. (range: 42-44° C.), aging for 1 hour at 43° C., then cooling linearly to 0° C. at 5° C./hr (about 9 hours). The solids are filtered and washed with water (750 L) at 10-20° C., and dried at <40° C. until KF<0.5%.

Concentration of betrixaban in mother liquors about 2-4 g/L. Concentration of betrixaban in wash liquors about 2 g/L. Yield about 90-95%.

Seed point temperature is above the saturation temperature for Form I at 90 g/L (saturates at about 47° C.). If a lower seed temperature is used, care must be taken to ensure there is no Form I generated.

Filtration temperature can be reduced to −10° C. for slight yield improvement (expect Mother Liquors losses to be reduced to about 1.4 g/L).

Particles are friable and drying is preferably performed with minimal agitation if possible.

Morphology variation has been observed; anneal cycle can be repeated if necessary to normalize morphology.

Example 8

Preparation of Betrixaban

Step 1:

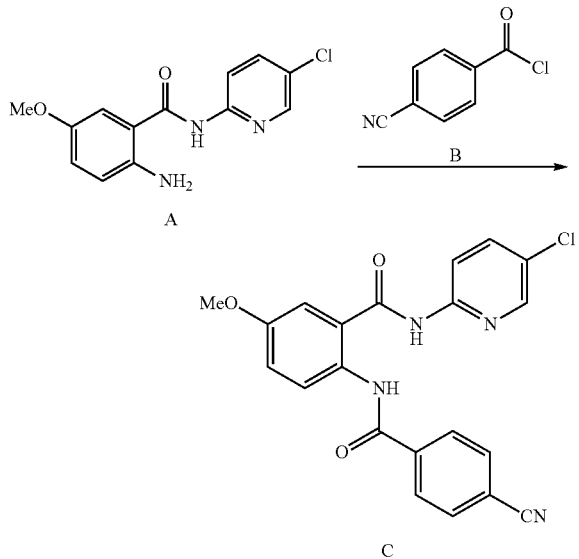

2-Amino-N-(5-chloro-pyridin-2-yl)-5-methoxy-benzamide (Compound A) is reacted with 4-cyanobenzoylchloride (Compound B, 1.1 eq.) in tetrahydrofuran in the presence of pyridine (0.4 eq.) at 19° C. to 25° C. Both Compound A and Compound B are commercially available or may be prepared according to know processes, for example, as described in U.S. Pat. No. 7,598,276, U.S. Patent Application Publication US 2010/0197929, both incorporated herein by reference in their entirety. The suspension is filtered and the filter cake is washed with ethanol. The solid obtained is dried under vacuum at 40° C. to afford the Compound C, N-(5-chloropyridin-2-yl)-2-(4-cyanobenzoylamino)-5-methoxybenzamide hydrochloride (In-Process Controls: HPLC analysis-specification<2% Compound A).

Step 2:

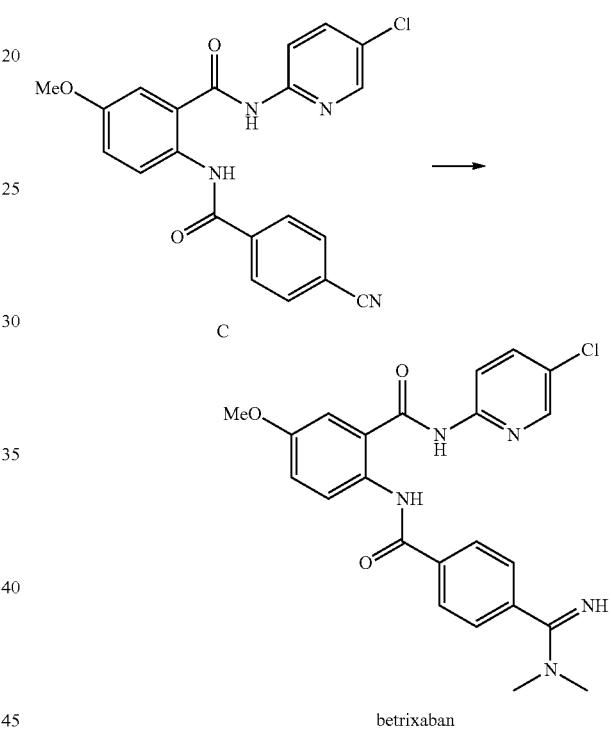

To the tetrahydrofuran solution of 2 M dimethylamine (4.7 eq. of Compound C), 2.3 M hexane solution of hexyllithium (5.05 eq. of Compound C) is slowly added over a period of at least three (3) hours while maintaining the temperature between 8° C. and 12° C. This solution is added to the tetrahydrofuran solution of Compound C while maintaining the temperature between −8° C. and −12° C. After completion of the reaction is confirmed by HPLC (Compound C<1% AUC) the solution temperature is adjusted to between −8° C. and 3° C. The reaction mixture is slowly added to the cold solution (between −8° C. and 3° C.) of aqueous sodium bicarbonate and sodium carbonate solution and stirred for at least 3 hours, maintaining the temperature between 19° C. and 25° C. The solid obtained is filtered and dried under vacuum to afford N-(5-chloropyridin-2-yl)-2-[4-(N,N-dimethyl-carbamimidoyl)-benzoylamino]-5-methoxy-benzamide (betrixaban) as a pale yellow solid (In-Process Controls: HPLC analysis-specification<1% Compound C).

Example 9

Preparation of Betrixaban Maleate Salt

The isolated betrixaban free base is dissolved in ethanol/water (3.9:1 v/v), treated with maleic acid (2 eq.) and stirred for at least 1 hour at 22° C. The solution is filtered and concentrated under vacuum until a final volume reduction of 5.7×v/w is achieved. Water (2×v/w) is then added and the mixture is concentrated until a final volume reduction of 5.7×v/w is achieved, continuing until the molar ratio between the content of ethanol and the content of betrixaban maleate salt in the mixture is lower than or equal to 6. The temperature of the suspension of betrixaban maleate salt is cooled to 19° C.-25° C. and stirred for at least 2 hours. Betrixaban maleate salt is isolated by filtration, washed with water and dried under vacuum at maximum temperature of 40° C. until the content of water is lower than, or equal to 0.5% w/w by Karl Fischer to obtain Form I. In-Process Controls: Molar ratio of ethanol in betrixaban maleate salt by GC and Karl Fischer<6, water content by Karl Fischer≤0.5% w/w.

Example 10

Recrystallization to Form II of Betrixaban Maleate Salt

Form I maleate salt is dissolved in ethanol/water (35:65 v/v) at 45-60° C., then cooled to 45-50° C. Seed crystals of Form II maleate salt is added (0.05 eq.), and the suspension aged and cooled to <30° C. The crystals in the suspension are wet milled to reduce size, heated to a temperature of 40-45° C., and re-cooled to <25° C. Betrixaban maleate salt is isolated by filtration, washed with water and dried under vacuum at maximum temperature of 40° C. until the content of water is lower than, or equal to 0.5% w/w by Karl Fischer. In-Process Controls: Form II maleate salt seed; 0.01-0.05 eq., Water content by Karl Fischer≤0.5% w/w.

Example 11

Preparation of Betrixaban Free Base

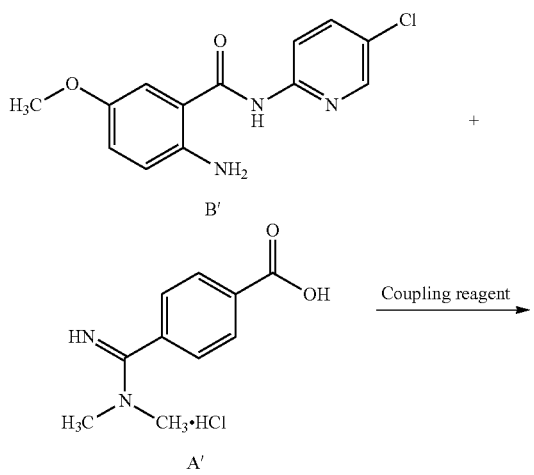

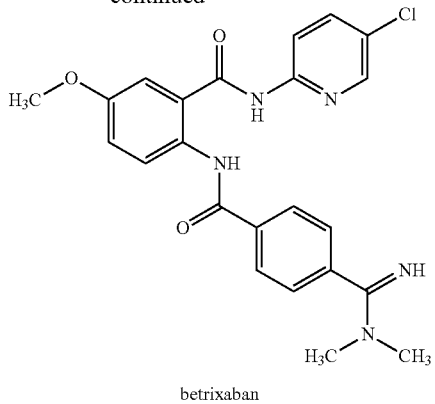

betrixaban

Compound B' (2.0 g), compound A' (1.98 g), 20 ml N,N-dimethylacetamide were added to a 100 ml round bottom flask, and stirred briefly for most of the solid to dissolve. Concentrated HCl (36 microliters) was then added. To this thin slurry was added 1-ethyl-3-(3'-dimethylaminopropyl) carbodiimide hydrochloride (EDC.HCl, Aldrich) (1.8 g total) in 3 portions, 0.6 g each, 20 min apart. The reaction mixture was stirred for 1.5 hours for complete reaction. Compounds A' and B' may be prepared according to methods described in U.S. application Ser. No. 12/969,371, filed on Dec. 16, 2010, titled "Methods of Synthesizing Factor Xa Inhibitors," which is hereby incorporated by reference in its entirety.

To this reaction mixture was added a solution of 2.3 g sodium carbonate in 10 mL water while the batch was cooled with water bath to keep the batch temperature 22-30° C. Then 10 mL water was added. The batch was stirred at 22-25° C. for 30 min. After a slurry was formed, 20 mL more water was added. The batch was stirred at 22° C. for 1 hour. The batch was filtered and the wet cake was washed with 3×5 mL water, then 5 ml acetone. The cake was dried on the funnel by suction. The weight of the dry cake is 2.95 g-2.92 g which is the crude betrixaban. To purify the crude betrixaban obtained, 1.0 g of the crude solid was mixed with 4 mL N,N-dimethylacetamide and heated to 70° C. for 30 min then added 8 ml toluene and heated for 30 min. The mixture was then cooled to 22° C. over 1 h, aged for 1 hour, then cooled to 0° C., aged at 0° C. for 2 hours, filtered, washed with 2×1 ml toluene. The cake was dried on the funnel by suction to obtain 0.88 g pure betrixaban.

Although the foregoing has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A crystalline form of betrixaban maleate, which is Form II, having an X-ray powder diffraction pattern having at least the following characteristic peak locations of 10.1, 14.6, 18.0, and 22.0 degrees 2θ (each ±0.1 degrees 2θ).

2. The crystalline form of claim 1, wherein the X-ray powder diffraction pattern has at least eight characteristic peak locations selected from 10.1, 14.6, 18.0, 19.6, 22.0, 23, 23.7, 24.5, 29.2, 29.5, 30.4, and 35.0 degrees 2θ (each ±0.1 degrees 2θ).

3. The crystalline form of claim 1, having an X-ray powder diffraction pattern approximate to the X-ray powder diffraction pattern shown in FIG. 2 or 3.

4. The crystalline form of claim 1, having a melting point of about 213° C.

5. The crystalline form of claim 1, having a unit cell containing two independent salt pairs of betrixaban and maleic acid wherein the imine N of betrixaban is protonated and forms an ionic H-bond to the maleic acid counter-ion.

6. The crystalline form of claim 1, characterized by a unit cell structure with the following cell parameters at 100 K: a=8.284 A, b=18.082 A, c=18.681 A, $\alpha$=71.22°, $\beta$=86.76°, $\gamma$=89.69°, and V=2645 A$^3$.

7. The crystalline form of claim 1, characterized by a unit cell structure with the following cell parameters at 273 K: a=8.419 A, b=18.113 A, c=18.73 A, $\alpha$=71.14°, $\beta$=86.71°, $\gamma$=89.31°, and V=2699 A$^3$.

8. A composition comprising a pharmaceutically acceptable carrier and the crystalline form of claim 1.

* * * * *